US008034592B2

(12) United States Patent (10) Patent No.: US 8,034,592 B2
Elias et al. (45) Date of Patent: Oct. 11, 2011

(54) FOSSIL FUEL-FREE PROCESS OF LIGNOCELLULOSIC PRETREATMENT WITH BIOLOGICAL HYDROGEN PRODUCTION

(75) Inventors: Dwayne Alexander Elias, Knoxville, TN (US); Melanie Rose Mormile, Rolla, MO (US); Matthew Brett Begemann, Madison, WI (US); Judy Davis Wall, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 33 days.

(21) Appl. No.: 12/635,328

(22) Filed: Dec. 10, 2009

(65) Prior Publication Data

US 2011/0136196 A1 Jun. 9, 2011

(51) Int. Cl.
*C12P 3/00* (2006.01)
*C12N 1/20* (2006.01)
*C12N 1/00* (2006.01)
*C12N 1/22* (2006.01)
*C12M 1/00* (2006.01)
*C12M 1/36* (2006.01)
*C12M 1/34* (2006.01)
*C12M 3/00* (2006.01)
*C12M 1/107* (2006.01)

(52) U.S. Cl. ............... 435/168; 435/252.3; 435/243; 435/252; 435/283.1; 435/286.6; 435/287.5; 435/289.1; 435/300.1

(58) Field of Classification Search ............... 435/168, 435/252.3, 243, 252, 283.1, 286.6, 287.5, 435/289.1, 300.1
See application file for complete search history.

(56) References Cited

U.S. PATENT DOCUMENTS

| 3,943,038 A | 3/1976 | Morinaga et al. |
| 6,013,494 A | 1/2000 | Nakamura et al. |
| 6,303,352 B1 | 10/2001 | Cameron et al. |
| 7,232,669 B1 | 6/2007 | Lin et al. |
| 2007/0207531 A1 | 9/2007 | Ferchichi et al. |

FOREIGN PATENT DOCUMENTS

WO WO 2006/119052 A2 * 9/2006

OTHER PUBLICATIONS

Tsai et al., *Haloanaerobium alcaliphilum* sp., an anaerobic moderate halophile from the sediments of great salt lake, Utah. Int. J. System. Bacteriol., 1995, vol. 45 (2): 301-307.*
Klinke et al., "Inhibition of ethanol-producting yeast and bacteria by degradation products produced during pre-treatment of biomass," Appl Microbiol Biotechol, 2004, 66: 10-26.
Bjerre et al., "Pretreatment of Wheat Straw Using Combined Wet Oxidation and Alkaline Hydrolysis Resulting in Convertible Cellulose and Hemicellulose," Biotechnology and Bioengineering, 1996, vol. 49, No. 5, pp. 568-577.

Dimitriu et al., "*Nitrincola lacisaponensis* gen. nov., sp. nov., a novel alkaliphilic bacterium isolated from an alkaline, saline lake," International Journal of Systematic and Evolutionary Microbiology, 2005, 55, 2273-2278.
Dimitriu et al., "Spatial and Temporal Patterns in the Microbial Diversity of a Meromictic Soda Lake in Washington State," Appl. Environ. Microbiol, 2008, vol. 74, No. 15, 4877-4888.
Bender at el., "Analysis of a Ferric Uptake Regulator (Fur) Mutant of *Desulfovibrio vulgaris* Hildenborough," Appl. Environ. Microbiol, 2007, vol. 73, No. 17, 5389-5400.
Elias et al., "Periplasmic Cytochrome c3 of *Desulfovibrio vulgaris* Is Directly Involved in H2-Mediated Metal but Not Sulfate Reduction," Appl. Environ. Microbiol, 2004, vol. 70, No. 1, 413-420.
Balch et al., "New Approach to the Cultivation of Methanogenic Bacteria: 2-Mercaptoethanesulfonic Acid (HS-CoM)-Dependent Growth of *Methanobacterium ruminantium* in a Pressurized Atmosphere," Appl. Environ. Microbiol, 1976, vol. 32, No. 6, 781-791.
Xie et al., "Cogeneration of hydrogen and methane from glucose to improve energy conversion efficiency," International Journal of Hydrogen Energy, 2008, 33, 5006-5011.
Levin et al., "Hydrogen production by *Clostridium thermocellum* 27405 from cellulosic biomass substrates," International Journal of Hydrogen Energy, 2006, 31, 1496-1503.
Mueller-Langer et al., "Techno-economic assessment of hydrogen production processes for the hydrogen economy for the short and medium term," International Journal of Hydrogen Energy, 2007, 32, 3797-3810.
Updegraff, "Semimicro Determination of Cellulose in Biological Materials," Analytical Biochemistry, 1969, 32, 420-424.
Lebo et al., "L," Kirk-Othmer Encyclopedia of Chemical Technology, John Wiley & Sons, Inc., New York, NY, 2001, vol. 15, pp. 1-32.
Datar et al., "Hydrogen production from the fermentation of corn stover biomass pretreated with a steam-explosion process," International Journal of Hydrogen Energy, 2007, 32, 932-939.
Liu et al., "Steam Pressure Disruption of Municipal Solid Waste Enhances Anaerobic Digestion Kinetics and Biogas Yield," Biotechnology and Bioengineering, 2002, vol. 77, No. 2, pp. 121-130.
Palmqvist et al., "Fermentation of lignocellulosic hydrolysates. II: inhibitors and mechanisms of inhibition," Bioresource Technology, 2000, 74, 25-33.
Palmqvist et al., "Fermentation of lignocellulosic hydrolysates. I: inhibition and detoxification," Bioresource Technology, 2000, 74, 17-24.

(Continued)

*Primary Examiner* — Ganapathirama Raghu
(74) *Attorney, Agent, or Firm* — Hovey Williams LLP

(57) ABSTRACT

The invention provides an isolated haloalkaliphilic microorganism designated as strain sapolanicus belonging to the genus *Halanaerobium*, which is capable of producing hydrogen from biomass. Methods of producing biohydrogen comprising the fermentation of the microorganism with alkaline pretreated biomass are also provided. Fermentation is preferably carried out without neutralization of the pretreated biomass and at a pH of greater than or equal to about 10.

14 Claims, 14 Drawing Sheets

OTHER PUBLICATIONS

Gaspar et al., "Corn fiber as a raw material for hemicellulose and ethanol production," Process Biochemistry, 2007, 42, 1135-1139.

Jackson, "Review Article " The Alkali Treatment of Straws, Animal Feed Science and Technology, 1977, 2, 105-130.

Spencer et al., "Rumen Microbial Degradation of Potassium Hydroxide-Treated Coastal Bermudagrass Leaf Blades Examined by Electron Microscopy," Journal of Animal Science, 1980, vol. 51, No. 5, 1189-1196.

Duckworth et al., "Phylogenetic diversity of soda lake alkaliphiles," FEMS Microbiology Ecology, 1996, 19, 181-191.

Jones et al., "Microbial diversity of soda lakes," Extremophiles, 1998, 2, 191-200.

Rees et al., "Diversity of Kenyan soda lake alkaliphiles assessed by molecular methods," Extremophiles, 2004, 8, 63-71.

Anderson, "Seasonal Characteristics of Two Saline Lakes in Washington," American Society of Limnology and Oceanography, 1958, vol. 3, No. 1, 51-68.

Pinkart et al., "The Sulfur Cycle in a Permanently Meromictic, Haloalkaline Lake," Proc. of SPIE, 2006, vol. 6309, 0277-786X.

Morimoto et al., "Overexpression of a hydrogenase gene in *Clostridium paraputrificum* to enhance hydrogen gas production," FEMS Microbiology Letters, 2005, 246, 229-234.

Sung et al., "Biological Hydrogen Production by Strict Anaerobic Bacteria: Fundamentals, Operational Strategies, and Limitations," Biocatalysis and Bioenergy, edited by Ching T. Hou and Jei-Fu Shaw, Copyright 2008 John Wiley and Sons, Chapter 15, pp. 265-287.

Sorokin et al., "Sulfur-Oxidizing Bacteria in Soap Lake (Washington State), a Meromictic, Haloalkaline Lake with an Unprecedented High Sulfide Content," Applied and Environmental Microbiology, 2007, vol. 73, No. 2, 451-455.

Eder et al., "Microbial Diversity of the Brine-Seawater Interface of the Kebrit Deep, Red Sea, Studied via 16S rRNA Gene Sequences and Cultivation Methods," Applied and Environmental Microbiology, 2001, vol. 67, No. 7, 3077-3085.

Perreault et al., "Characterization of the Prokaryotic Diversity in Cold Saline Perennial Springs of the Canadian High Arctic," Applied and Environmental Microbiology, 2007, vol. 73, No. 5, 1532-1543.

Rengpipat et al., "*Halobacteroides acetoethylicus* sp. nov., a New Obligately Anaerobic Halophile Isolated from Deep Subsurface Hypersaline Environments," System. Appl. Microbiol., 1988, 11, 28-35.

Hawkes et al., "Sustainable fermentative hydrogen production: challenges for process optimisation," International Journal of Hydrogen Energy, 2002, 27, 1339-1347.

Gavala et al., "Biological hydrogen production in suspended and attached growth anaerobic reactor systems," International Journal of Hydrogen Energy, 2006, 31, 1164-1175.

Miller et al., "Electricity generation by anaerobic bacteria and anoxic sediments from hypersaline soda lakes," Extremophiles, 2008, 12, 837-848.

GenBank: X89071.1: *H.acetoethylicum* gene for 16S ribosomal RNA, www.ncbi.nlm.nih.gov, Jun. 7, 1996.

GenBank: AJ309519.1: *Halanaerobium* sp. KT-2/3-3 16S rRNA gene, www.ncbi.nlm.nih.gov, Jun. 6, 2003.

GenBank: AM157647.1: *Halanaerobium* sp. AN-BI5B 16S rRNA gene, strain AN-BI5B, www.ncbi.nlm.nih.gov, Apr. 14, 2006.

Mormile et al., "*Halomonas campisalis* sp. nov., a Denitrifying, Moderately Haloalkaliphilic Bacterium," System. Appl. Microbiol., 1999, 22, 551-558.

Holladay et al., "An overview of hydrogen production technologies," Catalysis Today, 2009, 139, 244-260.

Hector et al., "Developing Yeast Strains for Biomass-to-Ethanol Production," Biomass Magazine, 2008, 3 pages.

Das et al., "Recent Developments in Biological Hydrogen Production Processes," Chemical Industry & Chemical Engineering Quarterly, 2008, 14 (2), 57-67.

Dien et al., "Bacteria engineered for fuel ethanol production: current status," Appl. Microbiol Biotechnol, 2003, 63, 258-266.

Tyler, "New Process Touted as Breakthrough for Cellulosic Ethanol," CleanTechnica, 2009, http:cleantechnica.com/files/2009/05/grass.jpg, 5 pages.

International Search Report dated Aug. 2, 2011, in corresponding PCT/US2010/057342 filed on Nov. 19, 2010.

Lin et al., "Enhancement of fermentative hydrogen/ethanol production from cellulose using mixed anaerobic cultures," International Journal of Hydrogen Energy, 2008, 33, 3660-3667.

Ueno et al., "Biological Production of Hydrogen from Cellulose by Natural Anaerobic Microflora," Journal of Fermentation and Bioengineering, 1995, vol. 79, No. 4, 395-397.

\* cited by examiner

SEQUENCE LISTING

```
<160> NUMBER OF SEQ ID NOS: 8

<210> SEQ ID NO 1
<211> LENGTH: 1191
<212> TYPE: DNA
<213> ORGANISM: Halanaerobium strain sapolanicus
<220> FEATURE:
<221> NAME/KEY: gene
<222> LOCATION: (1)..(1191)
<223> OTHER INFORMATION: 16S rRNA
<220> FEATURE:
<223> OTHER INFORMATION: Newly discovered organism that does not yet
      have a species designation, but is scientifically termed strain
      sapolanicus
<220> FEATURE:
<221> NAME/KEY: misc_feature
<222> LOCATION: (621)..(621)
<223> OTHER INFORMATION: n is a, c, g, or t

<400> SEQUENCE: 1
ggaagccttc gggcggaaga cgagactaga tagtggcgga cgggtgagta acacgtggat      60
aacctgtcct caagtctggg ataacctggc gaaagtcggg ctaatcccgg gtaagctgag     120
agtgtggcat cacacaatca gaaaaggtgc tattagcatc gtttgaggag gggtccgcgg     180
tagattagct agctggtgag gtaatggctc accagggcga caatctatag ctggtctgag     240
aggacgatca gtcacactgg aactgagaca cggtccagac tcctacggga ggcagcagtg     300
gggaatcttc cacaatgggc gaaagcctga tggagcaacg ccgcgtgagt gaagaaggtc     360
ttaggattgt aaagctctgt ccttagggaa gaaccgtggg tatagaaaat gatacccacc     420
tgacggtacc tttggaggaa gcactggcta actacgtgcc agcagccgcg gtaatacgta     480
gagtgcaagc gttgtccgga attattgggc gtaaagggta cgcaggcgga taatcaagtc     540
aagcgtgaaa ggtgtcggct taaccgacag actgcgtttg aaactggtta tcttgagtgt     600
aacagaggag agtggaattc ntagtgtagt ggtgaaatac gtagatatta ggaagaacac     660
cagtggcgaa ggcgactctc tgggttaaca ctgacgctga ggtacgaaag ctgggggagc     720
gaacgggatt agataccccg gtagtcccag ccgtaaacga tggatactag gtgttggagg     780
ttcgaatcct tcagtgccgg agttaacgca ttaagtatcc cgcctgggga ttacgatcgc     840
aagattgaaa ctcaaaggaa ttgacggggg cccgcacaag cggtggagca tgtggtttaa     900
ttcgaagcaa cgcgaagaac cttaccgaga attgacatcc cgtgactacc tgtgaaagca     960
gggtttggca tttatgtcac acggagacag gtggtgcatg gctgtcgtca gctcgtgtcg    1020
tgagatgttg ggttaagtcc cgcaacgagc gcaacccctg ttcttagttg ccagcgagta    1080
atgtcgggga ctctaagaag actgccggtg aaagtcggag gaaggtgggg atgacgtcaa    1140
```

```
gtcctcatgc cctttatatc tcgggctaca cacgtgctac aatggttggt a            1191
```

<210> SEQ ID NO 2
<211> LENGTH: 1514
<212> TYPE: DNA
<213> ORGANISM: Halanaerobium sp. AN-B15B
<220> FEATURE:
<221> NAME/KEY: gene
<222> LOCATION: (1)..(1514)
<223> OTHER INFORMATION: 16S rRNA

<400> SEQUENCE: 2

```
agagtttgat catggctcag gacgaacgct ggcggcgtgc ttaacacatg caagtcgaac     60
ggtctacctc gacggaaacc ttcggggttga agacgagatc tagatagtgg cggacgggtg   120
agtaacacgt gaataatctg tcctcaagtc tgggataacc tggcgaaagt cgggctaatc   180
cgaggtaagc tgagagtgtg gcatcacaca atcagaaaag gtggctctgc catcgtttga   240
ggaggagttc gcggtagatt agctagctgg tgaggtaatg gctcaccagg caacaatct    300
atagctggtc tgagaggacg atcagtcaca ctggaactga gacacggtcc agactcctac   360
gggaggcagc agtgggaat cttccacaat gggcgaaagc ctgatggagc aacgccgcgt    420
gagtgaagaa ggtcttagga ttgtaaagct ctgtccttag gaagaaccg tgggtataga    480
aaatgatacc cacctgacgg tacctttgga ggaagcactg gctaactacg tgccagcagc   540
cgcggtaata cgtagagtgc aagcgttgtc cggaattatt gggcgtaaag gtacgcagg    600
cggataatca agtcaagcgt gaaggtgtc ggcttaaccg acagactgcg tttgaaactg    660
gttatcttga gtgtaacaga ggagagtgga attcctagtg tagtggtgaa atacgtagat   720
attaggaaga acaccagtgg cgaaggcgac tctctgggtt aacactgacg ctgaggtacg   780
aaagctgggg gagcaaacgg gattagatac cccggtagtc ccagccgtaa acgatggata   840
ctaggtgttg gaggttcgaa tccttcagtg ccggagttaa cgcattaagt atcccgcctg   900
gggattacga tcgcaagatt gaaactcaaa ggaattgacg ggggcccgca caagcggtgg   960
agcatgtggt ttaattcgaa gcaacgcgaa gaaccttacc gagaattgac atcccgtgac  1020
catctatgaa agtagaattt agcacttagt gttacacgga gacaggtggt gcatggctgt  1080
cgtcagctcg tgtcgtgaga tgttgggtta agtcccgcaa cgagcgcaac ccctattctt  1140
agttgccagc gagtaatgtc ggggactcta agaagactgc cggtgaaagt cggaggaagg  1200
tggggatgac gtcaagtcct catgcccttt atatctcggg ctacacacgt gctacaatgg  1260
ctgatacaga ggggagcaaa gctgcgaagt ggagcaaatc ctttaaaatc agtcccagtt  1320
cggattgcag gctgcaactc gcctgtatga agttggaatc gctagtaatc gcaggtcagc  1380
atactgcggt gaatacgttc ccgggccttg tacacaccgc ccgtcacacc aatcgagttg  1440
gatgcaccag aagtcatctg cggatgccaa aggtgtgtcc ggtaagaggg gtgaagtcgt  1500
aacaaggtaa ccgt                                                    1514
```

<210> SEQ ID NO 3
<211> LENGTH: 20
<212> TYPE: DNA
<213> ORGANISM: Artificial Sequence
<220> FEATURE:
<223> OTHER INFORMATION: universal bacterial primer 27F

<400> SEQUENCE: 3

```
agagtttgat cctggctcag                                                 20
```

```
<210> SEQ ID NO 4
<211> LENGTH: 19
<212> TYPE: DNA
<213> ORGANISM: Artificial Sequence
<220> FEATURE:
<223> OTHER INFORMATION: universal bacterial primer 1492R

<400> SEQUENCE: 4
ggttaccttg ttacgactt                                               19

<210> SEQ ID NO 5
<211> LENGTH: 20
<212> TYPE: DNA
<213> ORGANISM: Artificial Sequence
<220> FEATURE:
<223> OTHER INFORMATION: universal archaeal primer 21F

<400> SEQUENCE: 5
ttccggttga tcctgccgga                                              20

<210> SEQ ID NO 6
<211> LENGTH: 18
<212> TYPE: DNA
<213> ORGANISM: Artificial Sequence
<220> FEATURE:
<223> OTHER INFORMATION: universal archaeal primer 23SaRev

<400> SEQUENCE: 6
ctttcggtcg cccctact                                                18

<210> SEQ ID NO 7
<211> LENGTH: 1471
<212> TYPE: DNA
<213> ORGANISM: Halanaerobium sp. KT-2/3-3
<220> FEATURE:
<221> NAME/KEY: gene
<222> LOCATION: (1)..(1471)
<223> OTHER INFORMATION: 16S rRNA

<400> SEQUENCE: 7
ggacgaacgc tggcggcgtg cttaacacat gcaagtcgaa cggtctacct cgacggaaac    60
cttcgggttg aagacgagat ctagatagtg gcggacgggt gagtaacacg tgaataatct   120
gtcctcaagt ctgggataac ctggcgaaag tcggctaat  ccgaggtaag ctgagagtgt   180
ggcatcacac aatcagaaaa ggtggctctg ccatcgtttg aggaggagtt cgcggtagat   240
tagctagctg gtgaggtaat ggctcaccag ggcaacaatc tatagctggt ctgagaggac   300
gatcagtcac actggaactg agacacggtc cagactccta cgggaggcag cagtggggaa   360
tcttccacaa tgggcgaaag cctgatggag caacgccgcg tgagtgaaga aggtcttagg   420
attgtaaagc tctgtcctta gggaagaacc gtgggtatag aaaatgatac ccacctgacg   480
gtacctttgg aggaagcact ggctaactac gtgccagcag ccgcggtaat acgtagagtg   540
caagcgttgt ccggaattat tgggcgtaaa gggtacgcag cgataatc  aagtcaagcg   600 tgaaaggtgt cggcttaacc gacagactgc gtttgaaact ggttatcttg agtgtaacag   660
aggagagtgg aattcctagt gtagtggtga aatacgtaga tattaggaag aacccagtgg   720
cgaaggcgac tctctgggtt aacactgacg ctgaggtacg aaagtgggga agcaacggga   780
ttagataccc cggtagtccc agccgtaaac gatggatact aggtgttgaa ggttcgaatc   840
cttcagtgcc ggagttaacg cattaagtat cccgcctggg gattacgatc gcaagattga   900
aactcaaagg aattgacggg ggcccgcaca agcggtggag catgtggttt aattcgaagc   960
aacgcgaaga accttaccga gaattgacat cccgtgacca tctatgaaag tagaatttag  1020
```

```
cacttagtgt tacacggaga caggtggtgc atggctgtcg tcagctcgtg tcgtgagatg      1080
ttgggttaag tcccgcaacg agcgcaaccc ctgttcttag ttgccagcga gtaatgtcgg      1140
ggactctaag aagactgccg gtgaaagtcg gaggaaggtg gggatgacgt caagtcctca      1200 tgcccttttat atctcgggct acacacgtgc tacaatggct gatacagagg ggagcaaagc     1260
tgcgaagtgg agcaaatcct ttaaaatcag tcccagttcg gattgcaggc tgcaactcgc     1320
ctgtatgaag ttggaatcgc tagtaatcgc aggtcagcat actgcggtga atacgttccc     1380
gggccttgta cacaccgccc gtcacaccaa tcgagttgga tgcaccagaa gtcatctgcg     1440
gatgccaaag gtgtgtccgg taagaggggt g                                    1471
```

<210> SEQ ID NO 8
<211> LENGTH: 1486
<212> TYPE: DNA
<213> ORGANISM: Halanaerobium acetethylicum
<220> FEATURE:
<221> NAME/KEY: gene
<222> LOCATION: (1)..(1486)
<223> OTHER INFORMATION: 16S rRNA

<400> SEQUENCE: 8

```
tggcggcgtg cttaacacat gcaagtcgaa cggtctacct cgacagaaac cttcgggttg       60
aagacgagat ctagatagtg gcggacgggt gagtaacacg tgaataatct gtcctcaagt      120
ccgggataac ctggcgaaag tcgggctaat ccggggtaag ctgagagtgt ggcatcacac      180
aatcagaaaa ggtggctctg ccatcgtttg aggaggagtt cgcggtagat tagctagctg      240
gtgaggtaat ggctcaccag gcaacaatc tatagctggt ctgagaggac gatcagtcac       300
actggaactg agacacggtc cagactccta cgggaggcag cagtgggaa tcttccacaa       360 tgggcgcaag cctgatggag caacgccgcg tgagtgaaga aggtcttagg attgtaaagc      420
tctgtcctta gggaagaacc gtggatgtag tcaatgacat ccacctgacg gtacctttgg      480
aggaagcact ggctaactac gtgccagcag ccgcggtaat acgtagagtg caagcgttgt      540
ccggaattat tgggcgtaaa gggtacgcag gcggataatc aagtcaagcg tgaaaggtgt      600
cggcttaacc gacagactgc gtttgaaact ggttatcttg agtgtaacag aggagagtgg      660
aattcctagt gtagtggtga aatacgtaga tattaggaag aacaccagtg gcgaaggcga      720
ctctctgggt taacactgac gctgaggtac gaaagctggg ggagcgaacg ggattagata      780
ccccggtagt cccagccgta aacgatggat actaggtgtt ggaggttcga atccttcagt      840
gccgagttta acgcattaag tatcccgcct ggggattacg atcgcaagat tgaaactcaa      900
aggaattgac gggggcccgc acaagcggtg gagcatgtgg tttaattcga gcaacgcga      960 agaaccttac cgagaattga catcccgtga ccatctatga gagtagagtt tggcacttag    1020
tgccacacgg agacaggtgg tgcatggctg tcgtcagctc gtgtcgtgag atgttgggtt    1080
aagtcccgca acgagcgcaa ccctgttcct agttgccag cgagtaatgt cggggactct    1140
aagaagactg ccggtgaaag tcggaggaag gtggggatga cgtcaagtcc tcatgccctt    1200
tatatctcgg gctacacacg tgctacaatg gctgatacag aggggagcaa agctgcgaag    1260
tggagcaaat ccttgaaaat cagtcccagt tcggattgca ggctgcaact cgcctgtatg    1320
aagttggaat cgctagtaat cgcaggtcag catactgcgg tgaatacgtt cccgggcctt    1380
gtacacaccg cccgtcacac caatcgagtt ggatgcacca gaagtcatct gcggatgcca    1440
aaggtgtgtc cggtaagagg ggtgaagtcg taacaaggta gccgta                   1486
```

FOSSIL FUEL-FREE PROCESS OF LIGNOCELLULOSIC PRETREATMENT WITH BIOLOGICAL HYDROGEN PRODUCTION

FEDERALLY SPONSORED RESEARCH OR DEVELOPMENT

This invention was made with government support under contract number 0132158, awarded by The National Science Foundation. The United States government has certain rights in the invention.

SEQUENCE LISTING

The following application contains a sequence listing in computer readable format (CRF), submitted as a text file in ASCII format entitled "40590," created on Dec. 10, 2009, as 9 KB. The contents of the text file are hereby incorporated by reference.

BACKGROUND OF THE INVENTION

1. Field of the Invention

The invention relates to a haloalkaliphilic hydrogen producing microorganism *Halanaerobium* sp. strain sapolanicus and methods of biohydrogen production using the same.

2. Description of Related Art

As the price of fossil fuels increases with diminishing reserves, biofuel production is seen as a viable contribution to current as well as future energy demands. Biohydrogen ($H_2$) and ethanol generation from microbial fermentation of plant materials holds promise, with $H_2$ having the advantage of producing only water vapor from combustion with oxygen.

Fibrous plant material is made up of lignocellulose and principally contains cellulose, hemicellulose and lignin. Cellulose and hemicellulose are more easily hydrolyzed, while lignin is recalcitrant to bacterial degradation. Thus, pretreatment of the biomass is necessary prior to microbial fermentation to separate the lignin from the cellulose and hemicellulose. The most common pretreatment method is steam blasting or steam explosion. Steam blasting requires electricity to produce the high heat and pressure necessary for steam generation, a usually natural gas- or coal-dependent step. As a consequence, considerable amounts of $CO_2$ are emitted by this process. Further, compounds that are inhibitory to the subsequent fermentation process are generated by lignin degradation, including weak acids, furan derivatives, and phenolic compounds, which must be removed in a separate detoxification step. Overall, the process of pretreatment steamblasting, detoxification, and subsequent fermentation is relatively inefficient and is still fossil fuel-dependent, thus counterproductive to the goal of reducing greenhouse gas emissions.

An effective alternative to steam blasting is alkali pretreatment of the lignocellulose. Acidic pretreatment methods are also known. Exposing the biomass to high pH separates cellulose and hemicellulose from the lignin, and reduces (breaks down) the crystalline cellulose structure thereby making it more accessible for degradation and fermentation while limiting production of inhibitory compounds or $CO_2$. However, the resulting substrate slurries are highly alkaline and have a potentially high concentration of salts, thus requiring a separate neutralization step prior to fermentation methods.

Microbial fermentation processes include both photofermentation and dark fermentation. Dark fermentation is the fermentative conversion of organic substrate to biohydrogen without the presence of light. The efficiency of dark fermentative production of $H_2$ depends on the pretreatment of the substrate and operating pH. In addition, most organisms are not suitable for extreme conditions such as high temperature, or extreme acidity or alkalinity. Thus, a neutral pH is preferred.

Although the potential exists for microbially generated fuels from biomass to be an economically viable energy substitute, several issues are still to be resolved. Existing processes still require energy input of steam blasting pretreatment of the raw biomass, detoxification of the resulting compounds that are inhibitory to fermentation, and overall have low hydrogen yields. In conventional biohydrogen production, 80-90% of the initial biomass remains in the form of volatile organic acids and solvents such as acetic, propionic, butyric acids, and ethanol. Thus, there is a need in the art for improved biohydrogen production methods that eliminate the need for steam blasting, detoxification, or pH neutralization.

BRIEF SUMMARY OF THE INVENTION

The present invention solves these problems by providing a novel, isolated microorganism strain sapolanicus of *Halanaerobium* and the mutants or derivatives thereof. The invention also provides a method of producing hydrogen by fermenting a source of carbon with the microorganism strain sapolanicus in a culture medium.

The invention also provides a novel, isolated hydrogen-producing microorganism, which is haloalkaliphilic, having a 16S rDNA sequence comprising SEQ ID NO: 1, or a sequence having at least 98% sequence homology with SEQ ID NO: 1. A method of producing hydrogen using this microorganism is also provided. The method comprises fermenting a source of carbon with the haloalkaliphilic, hydrogen-producing microorganism to produce hydrogen.

DETAILED DESCRIPTION OF THE INVENTION

Figure 1:
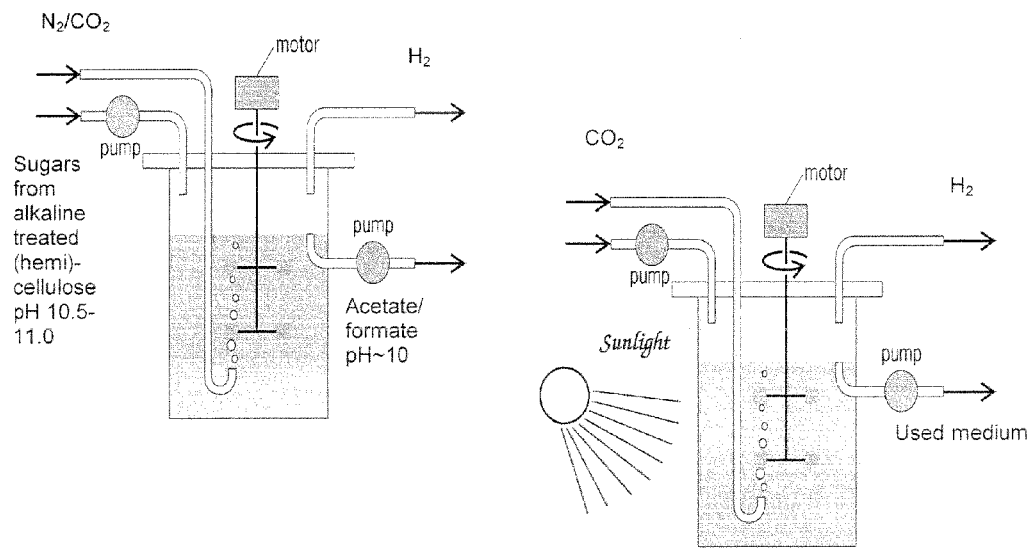
FIG. 1 illustrates a fermentation reactor and downstream photobioreactor.

The present invention provides a biomass pretreatment process that can be combined with the fermentative production of biohydrogen without the currently required steps of detoxification of lignin-derived degradation products or the neutralization step to decrease the solution/slurry pH to about 7. The present biohydrogen production method eliminates the need for steam blasting, thus reducing fossil fuel use for heat and reducing $CO_2$ generation, and also eliminates the need for removal of toxic lignin byproduct compounds. The inventive process is amenable to larger scale, commercial or industrial applications for the production of hydrogen as a biofuel from microbial fermentation of biomass. This is accomplished with no dependency on fossil fuels anywhere in the process. Not only is $CO_2$ not generated, but the process actually uses $CO_2$, thereby surpassing the standard of being carbon neutral while also representing a more streamlined and cost-effective process for biohydrogen production.

As used herein the term "biomass" refers to living and recently dead biological material and organic waste that can be used for fuel or for the production of fuel. Lignocellulosic biomass materials are particularly preferred. Examples include industrial and agricultural wastes, with seasonal grasses (e.g., switchgrass), agricultural products (e.g., straw, corn stover, seed cleanings, seed hulls, ground corn, wheat, wheat middlings, soybean hulls, dried distillers grains, oat hulls, milo, rye, oats, soybeans, alfalfa, canola, canola meal, safflowers, safflower meal, corn gluten feed), saw dust, municipal solid waste (e.g., paper, paperboard, food waste), waste from processing facilities for products such as sugar (e.g., beet pulp, sugar cane residue), fruit (e.g., seed, skin, pulp), or paper (e.g., paper products, wood pulp), and mixtures thereof being particularly preferred. The biomass may be solid, semi-solid, liquid, or in any other physical form and preferably comprises a source of carbon (e.g., the carbon substrate). Preferred carbon sources (e.g., sugars) include carbohydrates, more preferably lignocellulosic-derived carbohydrates, and even more preferably pentose and hexose sugars derived from cellulosic and hemicellulosic materials, and combinations thereof. Particularly preferred sugars are selected from the group consisting of cellobiose, glucose, ribose, xylose, arabinose, galactose, mannose, and combinations thereof.

The biomass is preferably subjected to an alkaline pretreatment process, followed by microbial fermentation of the aqueous pretreated biomass. Pretreatment is preferably carried out using a $Na_2CO_3$ alkaline reagent at about 4.25 g/L. The alkaline pretreatment process is also preferably carried out at temperatures of from about 20° C. to about 55° C., more preferably from about 35° C. to about 55° C., and pressures of about 1 atm. Advantageously, the biomass pretreatment process can be immediately followed by fermentation without neutralization or detoxification of the pretreated biomass feedstock.

Fermentation of the alkali-treated biomass is accomplished with a haloalkaliphilic microorganism capable of biohydrogen production under highly alkaline and hypersaline conditions. Thus, the invention also provides an isolated microorganism for use in the inventive biohydrogen production method. The isolated microorganism is a member of the genus *Halanaerobium*, and herein designated as strain sapolanicus (ATCC Patent Deposit Designation No. PTA-10410, deposited Oct. 13, 2009). Unlike other members of the *Halanaerobium* genus, the novel isolated microorganism is highly alkaliphilic with optimum growth at a pH of from about 10.5 to about 11. Suitable microorganisms for use with the inventive method preferably have a 16S ribosomal DNA (rDNA) sequence comprising SEQ ID NO: 1, or a 16S rDNA sequence having at least 98% sequence homology with SEQ ID NO: 1, and more preferably at least 99% sequence homology with SEQ ID NO: 1. Such microorganisms include mutants and derivatives (progeny) of the microorganism which retain the haloalkaliphilic properties of strain sapolanicus. Mutants (such as by deletion, insertion, and/or substitution of a base) include those occurring spontaneously in the passage or cultivation of the organism.

The alkali-treated feedstock is fermented with the microorganism in a culture medium under conditions suitable for hydrogen production. A preferred culture medium comprises (per liter): 70 g NaCl, 40 g $Na_2CO_3$, 6.3 g $K_2HPO_4$, 1 g yeast extract, 0.75 g $Na_2S$, and 0.6 g cysteine, along with 10 ml of basal medium stock solution and 10 ml of trace mineral solution. The basal medium stock solution preferably comprises 50 mg $NH_4NO_3$, 8.5 mg $MgCl_2.6H_2O$, 7.5 mg $SiO_2$, 4.5 mg $MnSO_4.H_2O$, 4.2 mg $CaCl_2.2H_2O$, 4 mg methylene blue, and 1.8 mg $FeSO_4.7H_2O$. The trace mineral solution preferably comprises (per liter): 3 g $MgSO_4.7H_2O$, 1.63 g $Na_3$-NTA, 1 g NaCl, 0.64 g $MnCl_2.4H_2O$, 0.13 g $ZnCl_2$, 0.1 g $FeSO_4.7H_2O$, 0.1 g $CaCl_2.2H_2O$, $CoCl_2.6H_2O$, 0.03 g $NiSO_4.6H_2O$, 0.025 g $Na_2MoO_4.2H_2O$, 0.025 g $Na_2WO_4.2H_2O$, 0.01 g $AlK(SO_4)_2.12H_2O$, 0.01 g $H_3BO_3$, and 7 mg $CuCl_7.2H_2O$.

The biomass feedstock comprising the carbon source is preferably provided at a concentration of from about 10 g/L to about 30 g/L, and preferably from about 20 g/L to about 25 g/L. The microorganism ferments the biomass feedstock to generate hydrogen gas (molecular hydrogen) along with other by-products (e.g., acetate). As mentioned, the method is preferably carried out without neutralization of the pretreated biomass (i.e., without decreasing the pH to about 7). That is, the pH of the pretreated feedstock (and resulting fermenting culture) is preferably greater than or equal to about 10, preferably from about 10 to about 11, and more preferably from about 10.5 to about 11. The salinity (% NaCl content) of the feedstock and fermenting culture is also preferably greater than or equal to about 7% w/v, and more preferably from about 7% to about 7.5% w/v. As used herein, the percentage "weight by volume" of the ingredient in the solution (referred to herein as "% w/v") is calculated based upon the total mass of the salt in grams per liter of the final solution where 1000 g/L is taken as 100% w/v. These pH and salinity conditions are preferably maintained in the culture medium throughout the fermentation process. That is, the pH of the fermenting culture preferably remains at or above about pH 10, and more preferably from about 10.5 to about 11, while the salinity remains greater than or equal to 7% w/v, and preferably from about 7% to about 7.5% w/v.

Fermentation is preferably carried out under substantially anaerobic conditions. As used herein, "substantially anaerobic conditions" refers to conditions where there no free oxygen available (e.g., less than about 0.1 ppm free oxygen, preferably from about 0 to about 0.1 ppm free oxygen), and includes naturally or artificially oxygen-depleted environments. More preferably, for artificial environments (i.e., test tube, fermentation reactor) a gas phase is provided in the headspace above the culture medium, with suitable gases being selected from the group consisting of $N_2$, $CO_2$, and mixtures thereof. A particularly preferred gas phase is a combination of about 80% $N_2$/20% $CO_2$. In a preferred method, the substantially anaerobic conditions can be maintained by sparging the culture medium with the selected gases.

The culture medium is also preferably agitated during fermentation, preferably at speeds of from about 100 rpm to about 250 rpm, and more preferably from about 200 rpm to about 250 rpm. Agitation can be accomplished via shaking, rotation, impeller, or any combination thereof. Fermentation also preferably proceeds in the absence of light (i.e., the culture is not exposed to any light sources during the fermentation process). Advantageously, this means that the biohydrogen process does not require light energy, and is capable of constantly producing hydrogen from organic compounds throughout the day and night. Fermentation is preferably carried out at a temperature of from about 30° C. to about 35° C., and preferably from about 30° C. to about 32° C., and for time periods of from about 100 hours to about 120 hours.

The fermentation process preferably results in a hydrogen molar yield (HMY) of from about 0.4 to about 2.3. Hydrogen molar yield is determined by measuring the moles of $H_2$ produced per mole of carbon oxidized. The hydrogen production rate preferably ranges from about 0.6 µmol $H_2$/hour/ml to about 8.8 µmol $H_2$/hour/ml. Hydrogen is preferably produced at a level of from about 15% to about 58% of the theoretical maximum yield. That is, the actual hydrogen yield in moles of hydrogen per mole of the relevant carbon source is expressed as a percentage of the maximum theoretically possible yield. For example, with glucose as the carbon source, a 100% yield indicates that the maximum theoretically possible yield of four moles of hydrogen is produced per one mole of glucose consumed.

Fermentation can be carried out in a fermentation apparatus (fermentation reactor). Suitable fermentation reactors are known in the art. In general, suitable apparatuses will have inlets for the biomass feedstock and gas for artificial atmosphere, and outlets for removing the hydrogen gas and by-products. The apparatus will contain the isolated microorganism and nutrient culture medium. The apparatus can also be equipped with a stir bar, impeller or other agitation device. The biomass may be continuously supplied to the fermentation apparatus as needed to keep up with the rate of fermentation of the biomass substrate. The fermentation apparatus may be a stand alone apparatus, or it may be combined with a downstream reactor for receiving and further processing the by-products (acetate, formate) from the fermentation apparatus. In one aspect, the fermentation apparatus may be coupled with a bioreactor comprising a culture medium of an alkaliphilic methanogen (e.g., *Methansalsum zhilinae*) to produce methane gas. In another aspect, the fermentation apparatus may be coupled with a photobioreactor comprising a culture medium of an alkaliphilic phototroph (e.g., *Ectothiorhoclospira vacuolata, E. shaposhnikovii, E. haloalkaliphila*) to produce additional hydrogen gas. FIG. 1 depicts an example of a fermentation reactor followed by a downstream photobioreactor.

The resulting hydrogen gas (from either the fermentation reactor or photobioreactor) can then be supplied to a hydrogen gas energy converting device. Such a device may convert hydrogen gas to energy via combustion of the hydrogen in the presence of oxygen to produce energy and water. In the alternative, electrochemical conversion may be utilized, such as in a fuel cell.

In yet a further embodiment, the waste stream from either the stand alone dark fermentation reactor or from the downstream photobioreactor could be recycled and reintroduced into the respective reactor since the salt concentration and pH would still be amenable to microbial cultivation. The pH or salt concentration may be adjusted, if necessary. Advantageously, this significantly reduces not only the amount of water required for the process, but the cost of the substrates for the cultivation and thereby the overall cost of the production of biohydrogen. Further, any biomass generated during the cultivation that would exit the reactors could be removed via centrifugation or other means, then dried and sold as carbon rich soil amendments. Thus, the present biohydrogen production method and isolated microorganism provides numerous advantages over existing biohydrogen production methods.

EXAMPLES

The following examples set forth preferred methods in accordance with the invention. It is to be understood, however, that these examples are provided by way of illustration and nothing therein should be taken as a limitation upon the overall scope of the invention.

Example 1

Isolation of Microorganism

The microorganism was found in the United States. The sampling site had a natural pH value of 10, a salt content ranging from 15-140 g NaCl/L of sample, and a high sulfide concentration ranging between 4.3-10.5 g/L. All plates and colony manipulations were carried out in a Coy anaerobic chamber (Coy Laboratory Products Inc., Grass Lake, Mich.) under an atmosphere of approximately 95% $N_2$/5% $H_2$.

Sediment samples were enriched using a culturing medium with glucose or cellobiose as the electron donor source. Serial dilution plating on medium containing 1.25% (wt./vol.) agar was then used to isolate single colonies and attain a pure culture.

Medium for enrichment included (per liter): 120 g NaCl, 1.12 g $Na_2B_4O_7$, 1.0 g $NH_4Cl$, 0.06 g $CaCl_2.2H_2O$, 0.05 g $MgCl_2.6H_2O$, 0.05 g $FeCl_2.6H_2O$, 0.79 g $C_3H_5O_3Na$, 0.58 g $C_2H_3O_2Na$, 0.85 g $NaNO_3$, 0.01 g KCl, 0.5 g tryptic soy broth, 0.5 g α-ketoglutaric acid, and 0.5 g disodium salt, along with 10 ml trace mineral solution. The trace mineral solution included (per liter): 6.0 mg $H_3BO_4$, 12.0 mg $CoCl_2.6H_2O$, 1.5 mg $CuCl_2.2H_2O$, 10.0 mg $MnCl_2.4H_2O$, 2.5 mg $NiCl_2.6H_2O$, 2.5 mg $Na_2MoO_4.2H_2O$, 7.0 mg ZnCl. The pH of the medium was raised to 10.0 with 1 N NaOH.

The culture medium for isolation was prepared by autoclaving the medium at 121° C. for 20 minutes. Next, 2-fold concentrated solutions of sterile medium were mixed with a 2-fold solution of agar in water. Sterile solutions of separate carbon sources, $Na_2S$, and cysteine were also added post-autoclaving. Cells and cell dilutions of liquid cultures were grown to an optical density of ~0.3 at 600 nm, and then aliquoted (1 ml) into empty, sterile plastic plates that had been equilibrated in the anaerobic chamber for at least 5 days. The culture medium included (per liter): 70 g NaCl, 40 g $Na_2CO_3$, 6.3 g $K_2HPO_4$, 1 g yeast extract, 0.75 g $Na_2S$, and 0.6 g cysteine, along with 10 ml of basal medium stock solution and 10 ml of trace mineral solution. The basal medium stock solution included: 50 mg $NH_4NO_3$, 8.5 mg $MgCl_2.6H_2O$, 7.5 mg $SiO_2$, 4.5 mg $MnSO_4.H_2O$, 4.2 mg $CaCl_2.2H_2O$, 4 mg methylene blue, and 1.8 mg $FeSO_4.7H_2O$. The trace mineral solution included (per liter): 3 g $MgSO_4.7H_2O$, 1.63 g $Na_3$-NTA, 1 g NaCl, 0.64 g $MnCl_2.4H_2O$, 0.13 g $ZnCl_2$, 0.1 g $FeSO_4.7H_2O$, 0.1 g $CaCl_2.2H_2O$, $CoCl_2.6H_2O$, 0.03 g $NiSO_4.6H_2O$, 0.025 g $Na_2MoO_4.2H_2O$, 0.025 g $Na_2WO_4.2H_2O$, 0.01 g $AlK(SO_4)_2.12H_2O$, 0.01 g $H_3BO_3$, and 7 mg $CuCl_2.2H_2O$.

Next, molten plating medium (50° C.) was poured over the cells, swirled and allowed to solidify. The plates were then incubated in the anaerobic chamber at 33° C. Single colonies were visible after approximately 2 weeks. Colonies were then extracted from agar with a sterile toothpick and inoculated into 2.5 ml of sterile liquid culture medium.

From biochemical analysis and staining, the isolate, designated as sapolanicus, was determined to be a gram negative, non-motile, non-sporulating, rod-shaped, obligate anaerobe.

Electron Microscopy

Cells were grown on 15 mM cellobiose in liquid culture under non-agitated conditions at 30° C. and pH 11 with 7% w/v NaCl. Cells were prepared for SEM observation by fixing with 2.5% (v/v) anaerobic glutaraldehyde. The fixed cells were allowed to sit for approximately 2 hours and then withdrawn by gentle removal of the tube stopper and the liquid, leaving the fixed cells in a small amount of liquid. The cells were then transferred onto a 0.22 µm pore size nucleopore filter (shiny side up). The membrane was positioned on top of a slightly moistened piece of filter paper in a small petri dish. Each solution was added to the filter paper only until the membrane began to float. The sample was washed with buffer twice (0.1 M cacodylate buffer), followed by 3 rinses with ultrapure water and, finally, an ethanol dehydration series of 10%, 20%, 35%, & 50% (v/v). Next, a second 0.22 µM pore size nucleopore filter was placed on top of the membrane with the sample and the dehydration continued with 70%, 90%, 95% and 3×100% (v/v) ethanol.

Figure 2:
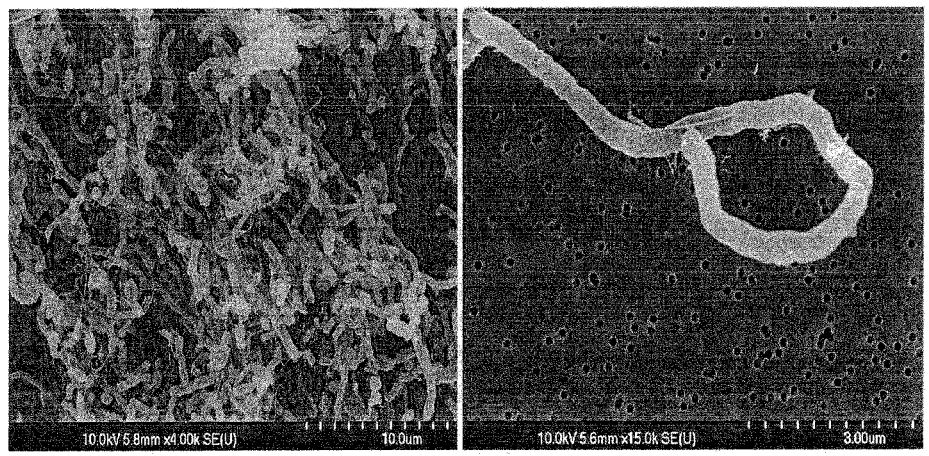
FIG. 2 is the scanning electron microscope (SEM) photographs of the isolated strain sapolanicus.

Following dehydration, the nucleopore filters were placed between screens and the sample was critical-point dried immediately (Tousimis Auto-Samdri; 815 Automatic Critical Point Dryer; Rockville, Md.). Next, the sandwiched nucleopore membranes were separated, mounted onto SEM stubs and sputter coated (Emitech K575x Turbo Sputter Coater; Kent, England) with a thin layer of palladium on a rotating sample holder (20 kV, 45 sec). The coated samples were then viewed using a Hitachi S-4700 FESEM (Hitachi High Technologies America, Inc.; Pleasanton, Calif.) at a working distance of 5-6 mm, a voltage of 2.0-10.0 kV, and a magnification of ~6000×. All cell preparations and visualization were conducted at the University of Missouri Electron Microscopy Core Facility (Columbia, Mo.). FIG. 2 shows the SEM photographs of the isolate, which is an elongated rod that is approximately 18×1 µm.

Figure 3:
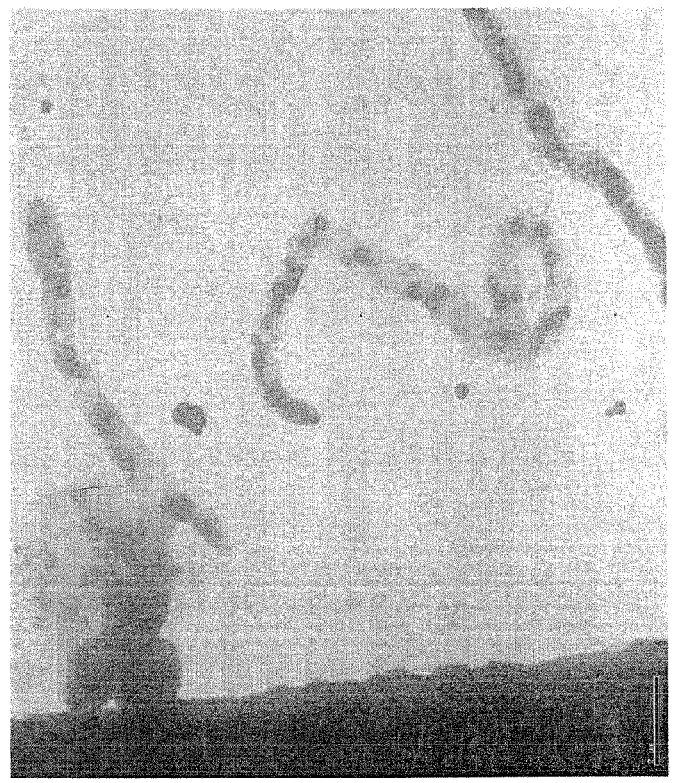
FIG. 3 is the transmission electron microscope (TEM) photographs of the isolated strain sapolanicus.
Figure 3:
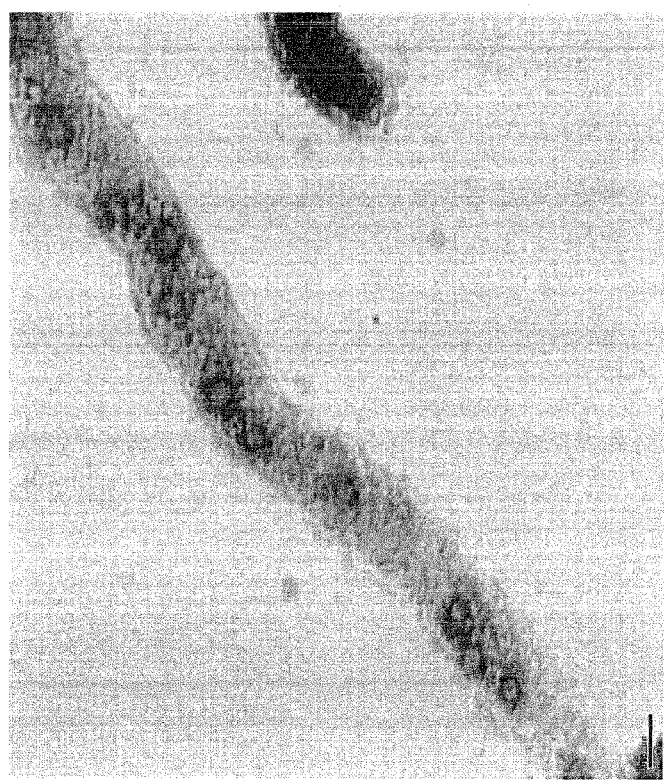

The cells were also viewed using TEM. Cells were grown as described above. The cells were pipetted onto TEM grids and stained with 2 mM uranyl acetate in 0.1 catecholate buffer (pH 7.4). The cells were viewed at 20 kV on the TEM. FIG. 3 shows the TEM photographs of the isolate.

16S rRNA Gene Sequence Analysis

Genomic DNA (gDNA) was isolated from frozen cell pellets. The cell pellet was thawed and resuspended in sterile deionized $H_2O$ (300 µl) with gentle pipetting, then boiled (10 min.) and centrifuged at 13,000×g for 3 minutes, at room temperature. The gDNA was purified with the Wizard® DNA purification kit (Promega, Madison, Wis.) according to the manufacturer's instructions. The supernatant (1 µl) containing purified gDNA was used for 16S rRNA gene amplification with universal bacterial primers 27F (SEQ ID NO: 3) and 14928 (SEQ ID NO: 4) as well as the universal archaeal primers 21F (SEQ ID NO: 5) and 23SaRev (SEQ ID NO: 6). PCR products were obtained for the bacterial, but not for the archaeal, PCR reactions.

The resultant bacterial PCR products were sequenced by the University of Missouri DNA Core Facility (Columbia, Mo.). The sequence was analyzed by BLAST analysis using the nucleotide collection and highly similar sequence (Megablast) settings. Analysis of the isolate's 16S rDNA sequence (GenBank Accession No. GQ215697; SEQ ID NO: 1) suggests that it is a member of genus *Halanaerobium*, with the closest significant matches being: 97.2% similarity with *Halanaerobium* sp. AN-B15B (GenBank Accession No. AM157647; SEQ ID NO: 2), 96.9% similarity with *Halanaerobium* sp. KT-2/3-3 (GenBank Accession No. AJ309519; SEQ ID NO: 7), and 96.4% similarity with *Halanaerobium acetethylicum* (GenBank Accession No. X89071; SEQ ID NO: 8). A major difference is that all reported members of this genus are neutrophilic, making strain sapolanicus unique in its alkaliphilicity, as demonstrated below.

pH and Salinity Experiments

Figure 4:
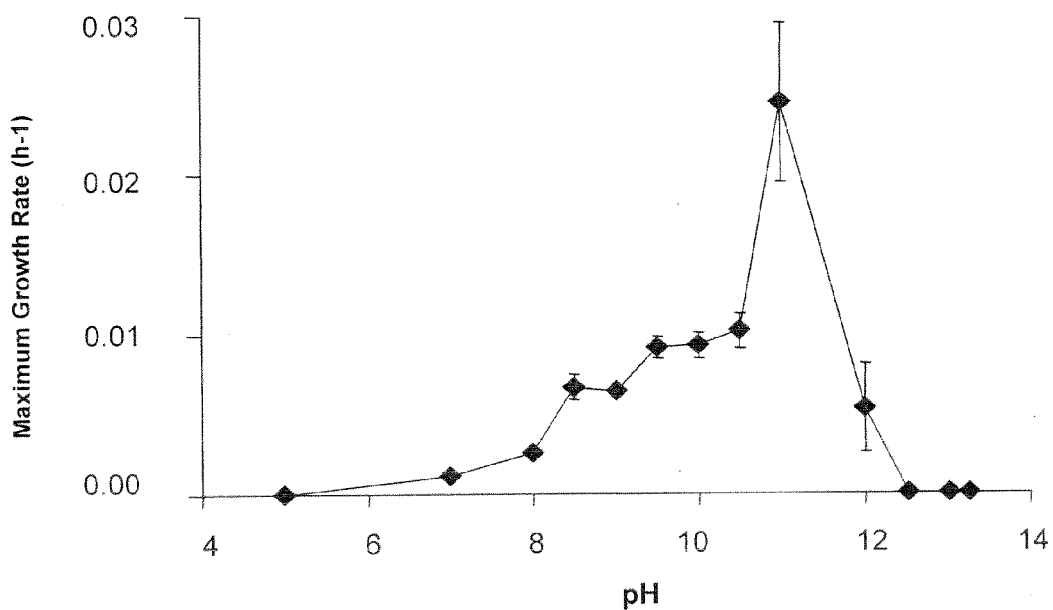
FIG. 4 illustrates the growth rate of isolated strain sapolanicus as a function of pH from Example 1.
Figure 5:
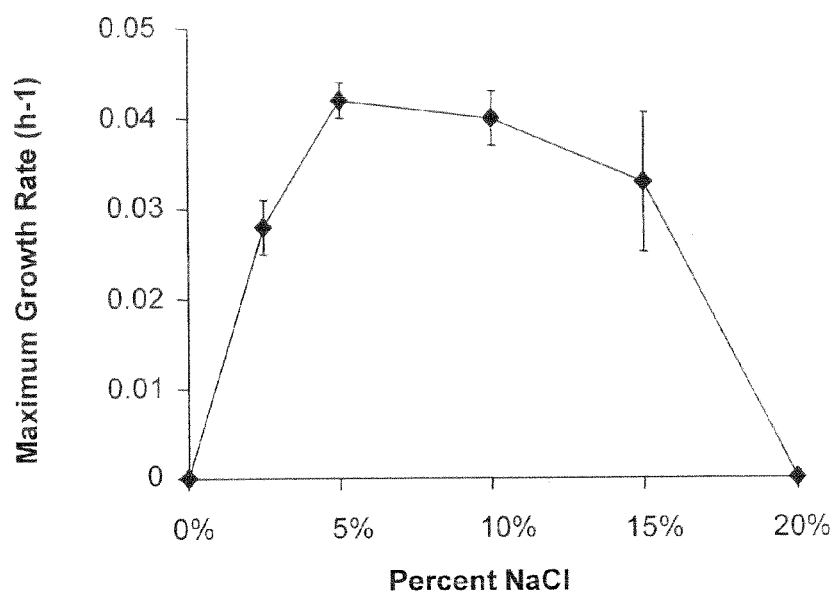
FIG. 5 illustrates the growth rate of isolated strain sapolanicus as function of NaCl concentration from Example 1.

The isolate sapolanicus was grown under conditions of increasing pH and salinity. For the pH tests, the isolate was grown using the culture medium described above at different pH ranging from 5 to 13.5. For the salinity tests, the isolate was tested at between about 0 to 20% w/v NaCL. FIGS. 4-5 show that the isolate is capable of growing at high pH and salinity. The optimum growth rate was observed at approximately pH 11, and about 7% w/v NaCl.

Example 2

Preparation of Culture Tubes with Sugar Substrates

Cultures were grown under anaerobic conditions in 28 ml Balch/Hungate tubes with a liquid volume of 5 ml capped with blue butyl rubber stoppers, crimp sealed with aluminum seals, and gassed with 80% $N_2$/20% $CO_2$. All medium components and sugars were purchased from either Sigma Life Science (St. Louis, Mo.) or Fisher Scientific (Pittsburgh, Pa.).

The empty tubes were first degassed, autoclaved at 121° C. for 20 minutes, and cooled to room temperature. Once cool, the culture medium described in Example 1 was added via filter sterilization using 0.2 µm syringe filters.

Stock solutions containing the carbon sources (sugars) were then filter-sterilized into the sterile culture tubes through 0.2 µm pore size syringe filters. The stock solutions of the carbon sources were prepared separately for each carbon source: cellobiose, glucose, mannose, ribose, galactose, arabinose, and xylose. The stock solutions were all used at a final concentration of 30 mM, except for cellobiose, which was used at 15 mM. Cultures with no carbon source (except the 0.1% v/v yeast extract) served as the negative control.

Culture volumes totaled 5 ml including a 10% (v/v) inoculation. Cultures were grown in triplicate in the dark at 30° C. A sample (0.3 ml) of each culture at pH ~10.5 was centrifuged at 13,000×g for 5 minutes at room temperature (20-22° C.), and the supernatant discarded. The pellet was resuspended in deionized and filter-sterilized (0.22 μm pore size) $H_2O$ to the original 0.3 ml volume and frozen at −20° C. until analyzed.

Example 3

Sugar Metabolism

In this Example, the growth and metabolic by-products of the sugar cultures prepared in Example 2 were measured under non-agitating conditions at 30° C., and pH 11, with 7% (v/v) NaCl. Growth was followed by optical density as well as by protein quantification. Protein concentration was determined using a modified Bradford assay. Hydrogen molar yield (HMY) was then calculated. For all tests, the time-dependent $H_2$ generation was quantified on a Gas Chromatogram (Varian Inc., Palo Alto, Calif.; Model CP-3380) equipped with a Varian fused Silica Select Permanent Gas/$CO_2$ HR column (CP-7430), operating at 30° C., and a thermal conductivity detector at 175° C. The carrier gas was $N_2$ at 14 psi, and samples were analyzed using a Star Chromatography Workstation Version 5.50 software (Varian, Inc.). Injection volumes were 50 μl with the injection port temperature at 50° C.

The loss of the carbon source and appearance of organic acids was followed over time with High Pressure Liquid Chromatography (HPLC; Shimadzu, Inc., Columbia, Md., USA), equipped with an Aminex HPX-87H Ion Exclusion column (125-0140; Phenomenex Inc., Torrance, Calif.) and a column oven (Shimadzu CTO-20A) set at 53° C. Both a Refractive Index Detector (Shimadzu RID-10A) and UV/VIS Detector (Shimadzu SPD-20A) were employed. Injection volumes for HPLC, 10 μl, were accomplished with an autosampler (Shimadzu SIL-10AF) and system controller (Shimadzu SCC-10A). The mobile phase for all detections was N, degassed 30 mM $H_2SO_4$ under isocratic flow (Shimadzu DGU-20A3) pumped (Shimadzu LC-10Ai) at 22 ml/min. All data from triplicate analyses were analyzed using Shimadzu LC Solutions Version 1.2

The procedures for the modified Bradford assay was as follows. A Bradford stock reagent was prepared in-house by first mixing a stock solution of 0.6 g of Brilliant Blue G250, 300 ml of Alcohol, and 600 ml of 85% phosphoric acid. Next, 150 ml of the stock solution was added to 850 ml of water. The solution was filtered through a 18.5 cm filter, and then stored in the dark until use. A 10 mg/ml BSA stock solution was prepared by mixing either 50 or 100 mg of Bovine Albumin (Fraction V; Sigma, St. Louis) with 5 or 10 ml of water, respectively (this stock can be further diluted to 1 mg/ml BSA, as necessary). The BSA stock was stored at −20° C. until use.

For the Bradford assay, the 0.3 ml samples were thawed and amended with 0.1 ml of 0.5N NaOH, heated to 80° C. for 3 minutes, cooled and then added to 4 ml of Bradford stock reagent. The resulting solution was mixed and then incubated at room temperature for 20 minutes. The solution is then mixed again and read at 595 nm using a tube of 0.3 ml of water with 0.1 ml of NaOH as the blank. Tubes for each culture are prepared in duplicate. A 0.3 ml BSA control (standard curve) was prepared by mixing 0.1 ml of 0.5 N NaOH and 1 mg/ml BSA stock solution. Tubes were set up as follows.

| Tube | 1 | 2 | 3 | 4 | 5 | 6 | 7 | 8 | 9 | 10 | 11 | 12 |
|---|---|---|---|---|---|---|---|---|---|---|---|---|
| NaOH | 0.1 | 0.1 | 0.1 | 0.1 | 0.1 | 0.1 | 0.1 | 0.1 | 0.1 | 0.1 | 0.1 | 0.1 |
| $H_2O$ | 0.30 | 0.295 | 0.290 | 0.285 | 0.280 | 0.275 | 0.270 | 0.265 | 0.260 | 0.250 | 0.240 | 0.230 |
| BSA | 0.00 | 0.005 | 0.010 | 0.015 | 0.020 | 0.025 | 0.030 | 0.035 | 0.040 | 0.050 | 0.060 | 0.070 |
| BSA | 0 μg | 5 | 10 | 15 | 20 | 25 | 30 | 35 | 40 | 50 | 60 | 70 |

Then 4 ml of Bradford reagent was added to each tube. The solution was incubated for 20 minutes at room temperature. Each solution was then mixed and the optical density was read at 595 nm using the tube containing only 0.3 ml water as the blank.

The results are provided in Table 1 below.

TABLE 1

Metabolic Profile under Non-agitation conditions

| Initial Substrate | Final Whole Cell Protein (μg/ml) | Final Optical Density (600 nm) | % $H_2$ in headspace | Hydrogen Molar Yield | Acetate (mM) | Formate (mM) |
|---|---|---|---|---|---|---|
| 0.1% Yeast Extract | 12 ± 6 | 0.06 ± 0.01 | 0.4 ± 0.5 | — | 4.3 ± 0.1 | 0 |
| 15 mM Cellobiose | 83 ± 5 | 0.29 ± 0.03 | 38 ± 2 | 2.3 ± 0.2 | 31.3 ± 0.6 | 7.9 ± 0.4 |
| 30 mM Glucose | 91 ± 2 | 0.33 ± 0.03 | 31 ± 2 | 1.9 ± 0.1 | 25.7 ± 0.6 | 0 |
| 30 mM Ribose | 91 ± 4 | 0.26 ± 0.01 | 13 ± 1 | 0.7 ± 0.1 | 24 ± 2 | 0 |
| 30 mM Xylose | 73 ± 6 | 0.17 ± 0.01 | 8.2 ± 0.5 | 0.5 ± 0.1 | 17 ± 1 | 0 |
| 30 mM Arabinose | 59 ± 1 | 0.15 ± 0.01 | 7 ± 2 | 0.4 ± 0.1 | 14 ± 3 | 0 |
| 30 mM Galactose | ND | ND | 16 ± 1 | 0.9 ± 0.1 | 14.7 ± 0.6 | 0 |
| 30 mM Mannose | ND | ND | 29 ± 5 | 1.7 ± 0.3 | 26 ± 3 | 0 |

ND—Not determined, although growth occurred.

All measurements were determined at the exhaustion of the carbon and electron source. All cultivations used a 5 ml culture with 23 ml of headspace of 80% $N_2$/20% $CO_2$ (v/v).

Figure 6:
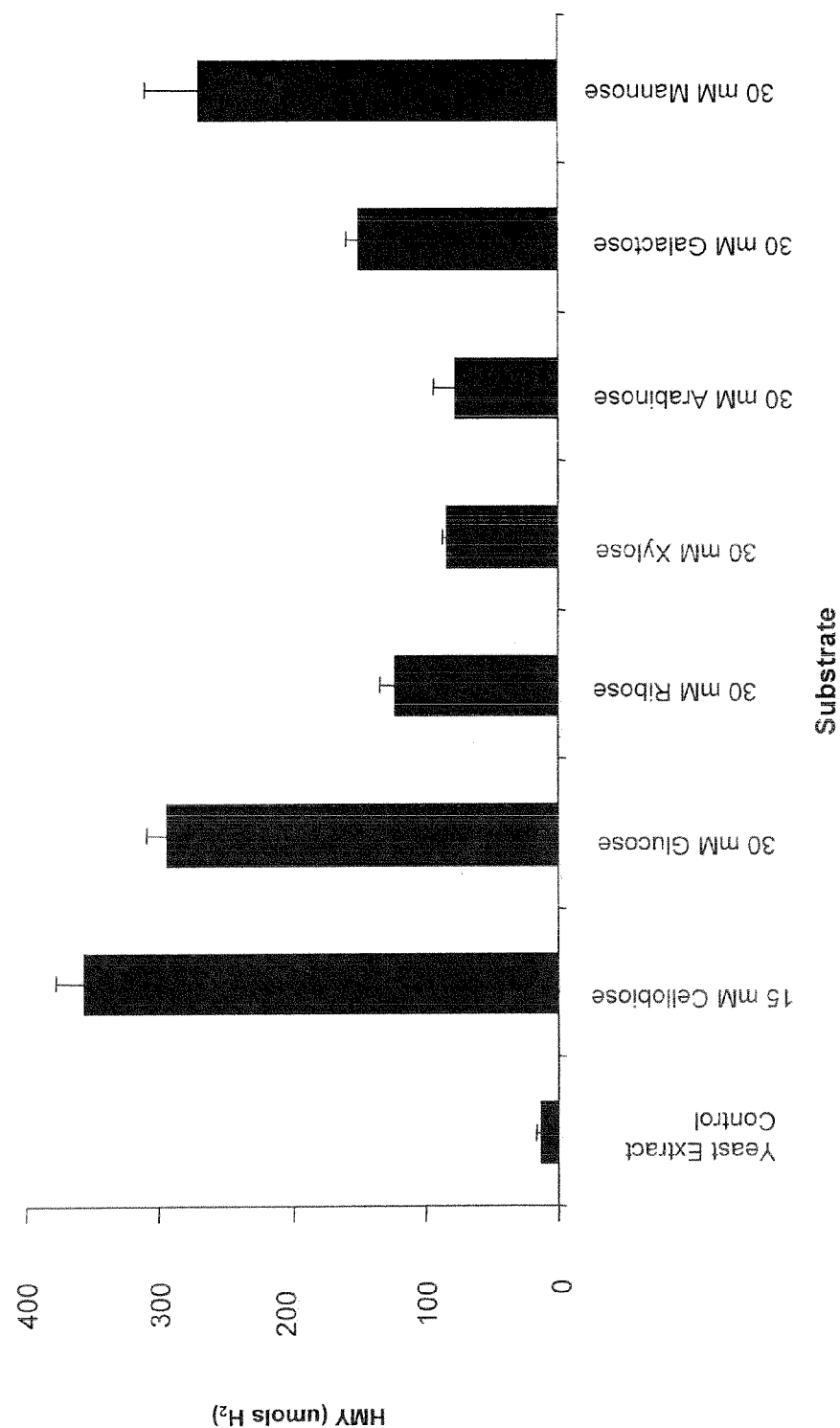
FIG. 6 shows the hydrogen production of isolated strain sapolanicus via fermentation of various cellulose- and hemicellulose-derived sugars from Example 3.

All tested sugars supported growth with average cell generation times of 20±1 h for glucose and 17±1 h for cellobiose under non-agitation conditions. Hydrogen was produced from all cultures and resulted in atmospheric concentrations of 7-12% hydrogen from 5-carbon sugars and 17-38% with 6-carbon sugars. FIG. 6 shows the hydrogen yield via fermentation of each sugar.

Figure 7:
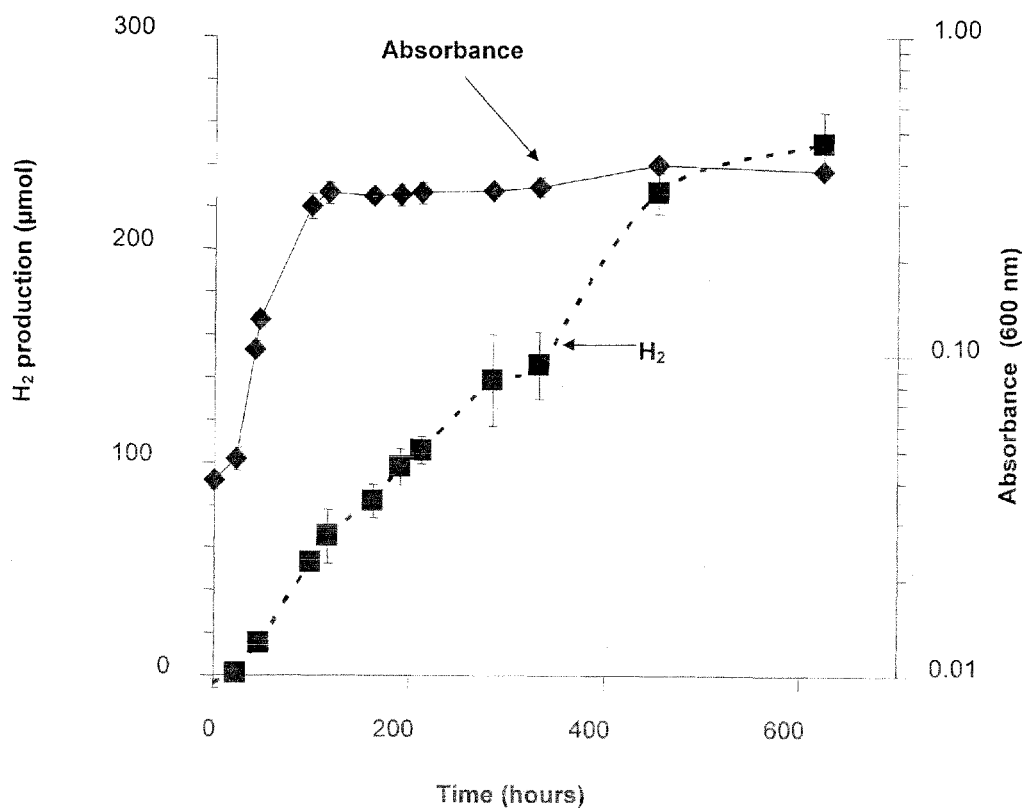
FIG. 7 depicts the growth rate and hydrogen production of isolated strain sapolanicus on cellobiose from Example 3.
Figure 8:
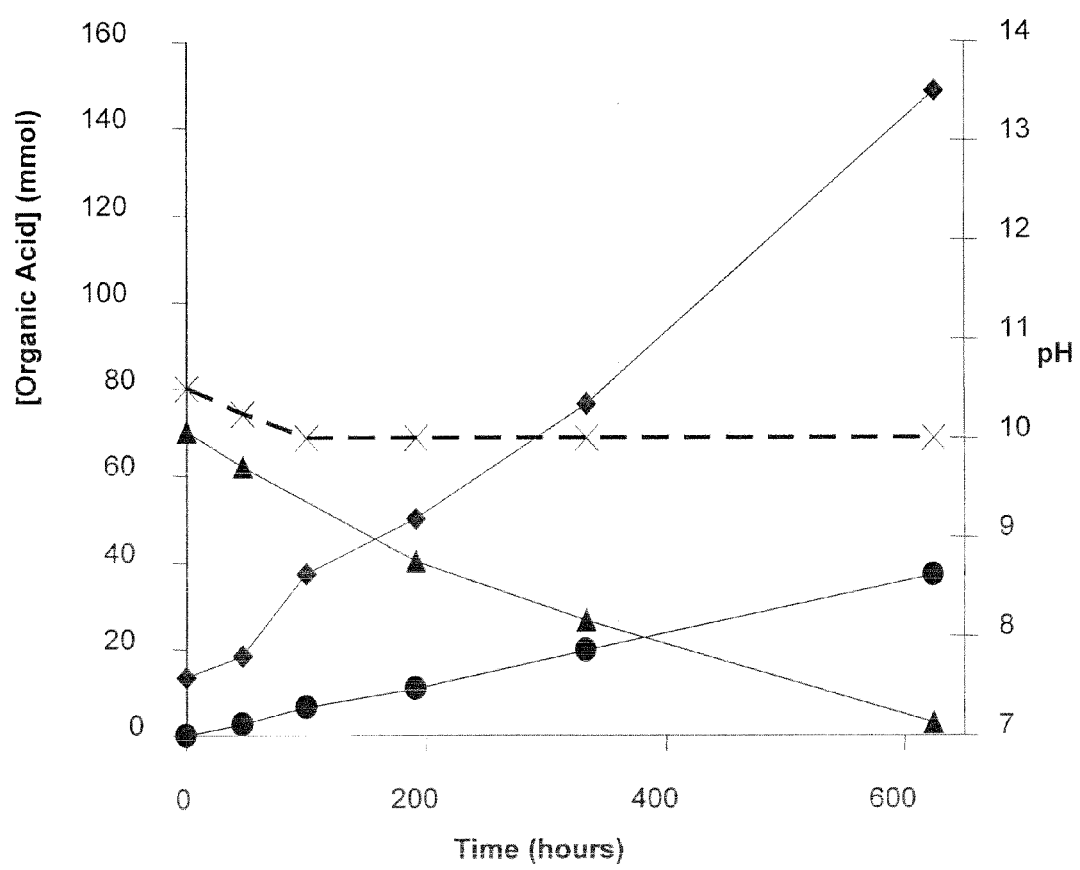
FIG. 8 illustrates the by-products generated by isolated strain sapolanicus on cellobiose at a high pH from Example 3.

The results for cellobiose are shown in FIGS. 7-8. As shown in FIG. 7, logarithmic growth (as measured by absorbance, ♦) occurred for the first 125 hours, at which point the cells entered stationary phase. However, hydrogen production (■) continued beyond 600 hours. As shown in FIG. 8, the production of acetate (♦) and formate (●) continued beyond 600 hours as well until cellobiose (▲) was exhausted. The pH (x) of the culture initially decreased from 10.5 but never fell below 10.0.

Figure 9:
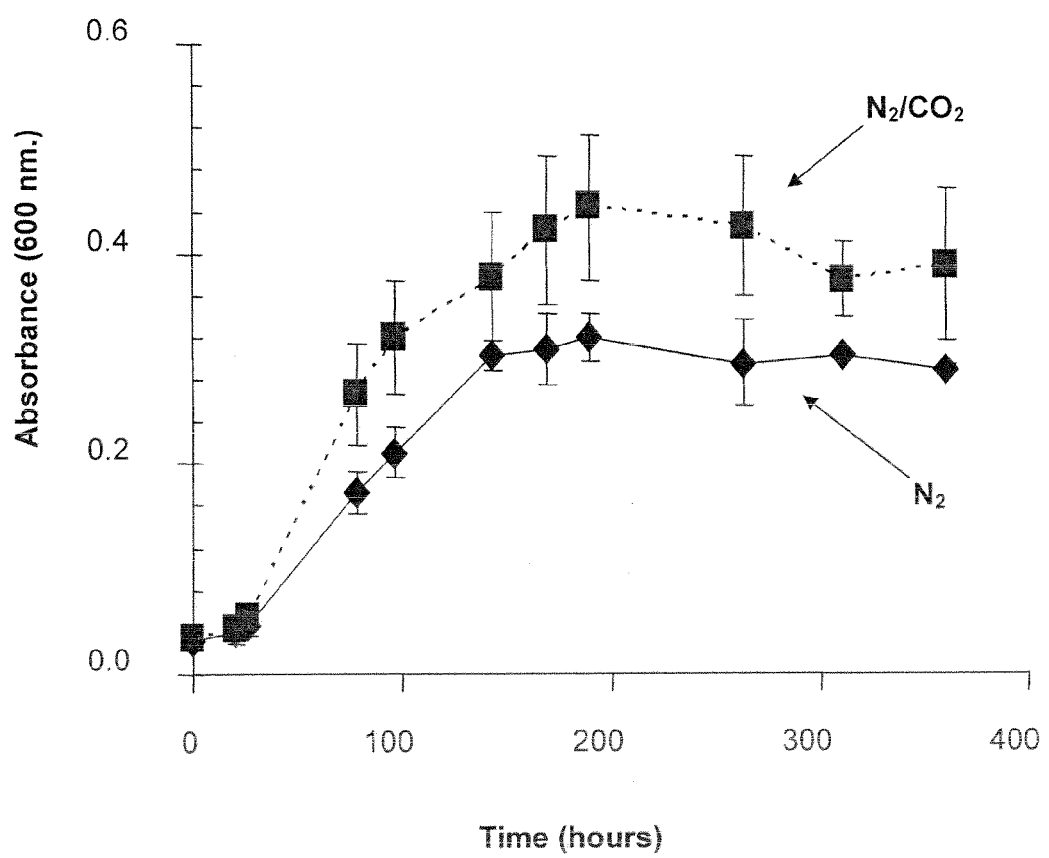
FIG. 9 is a graph of the growth rate of isolated strain sapolanicus under cultivation conditions having $CO_2$ headspace in the culture tube and in the absence of $CO_2$ headspace from Example 3.
Figure 10:
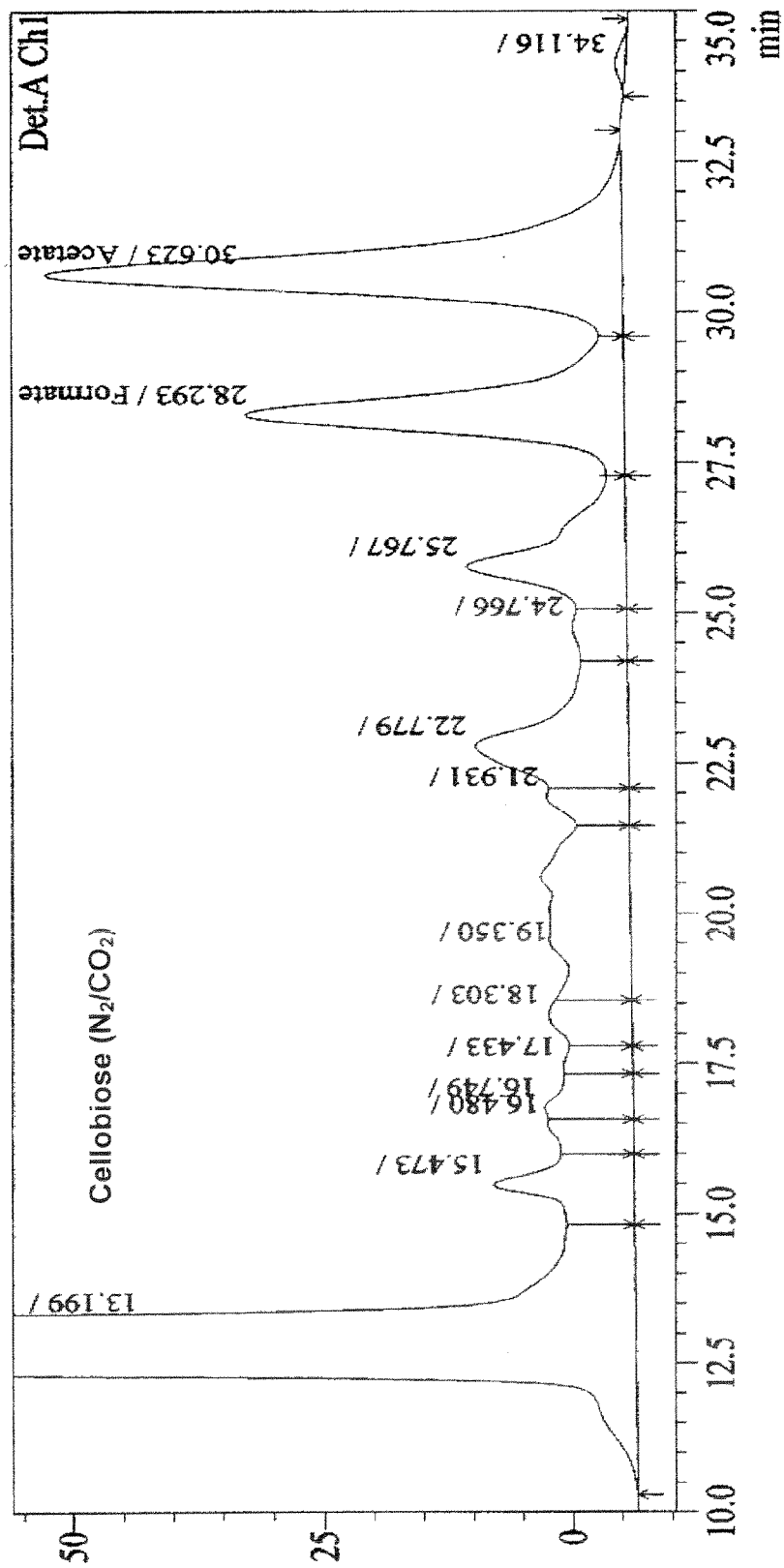
FIG. 10 illustrates the metabolic profile of isolated strain sapolanicus on cellobiose in the culture tube having $CO_2$ headspace from Example 3.
Figure 11:
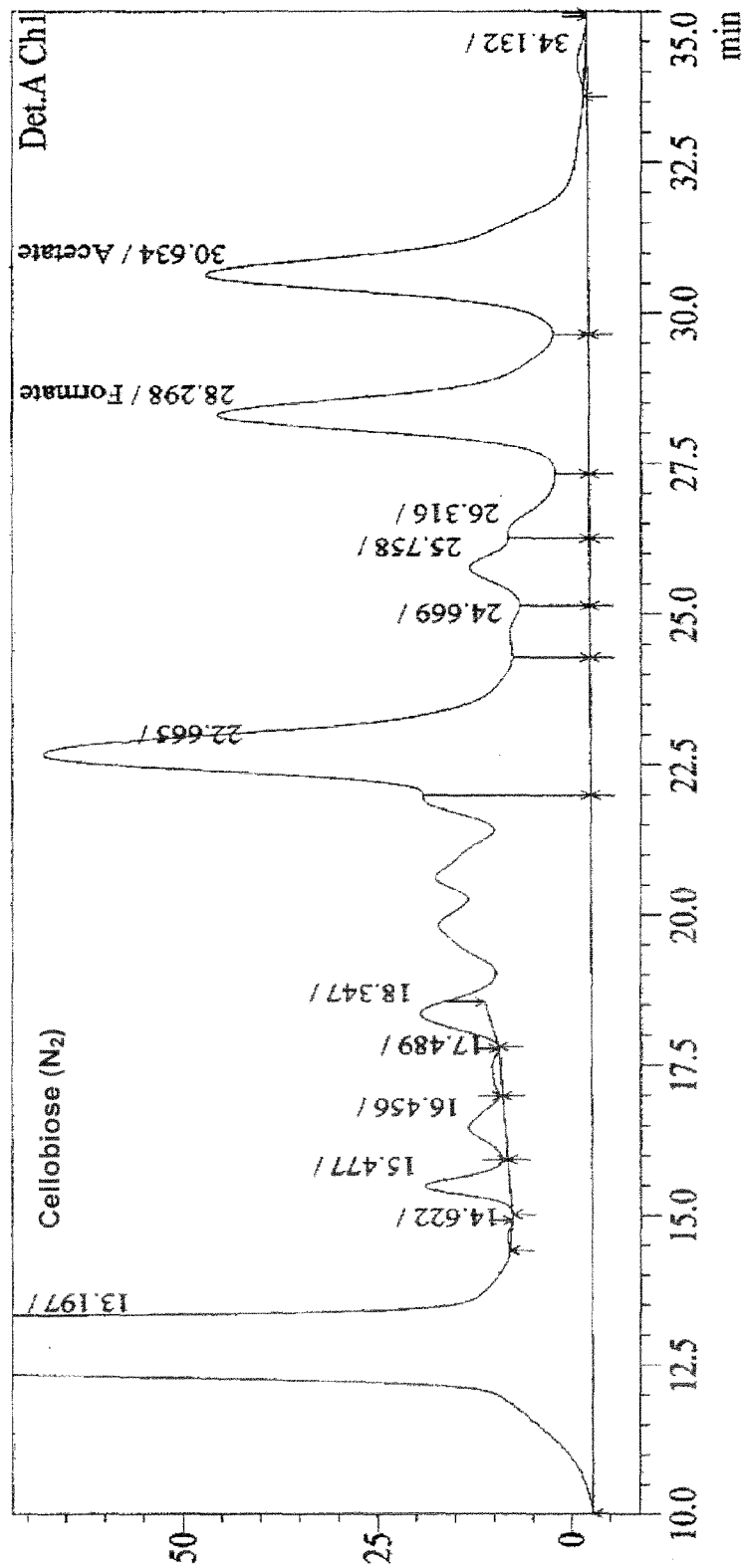
FIG. 11 illustrates the metabolic profile of isolated strain sapolanicus on cellobiose in the culture tube having in the absence of $CO_2$ headspace from Example 3.
Figure 12:
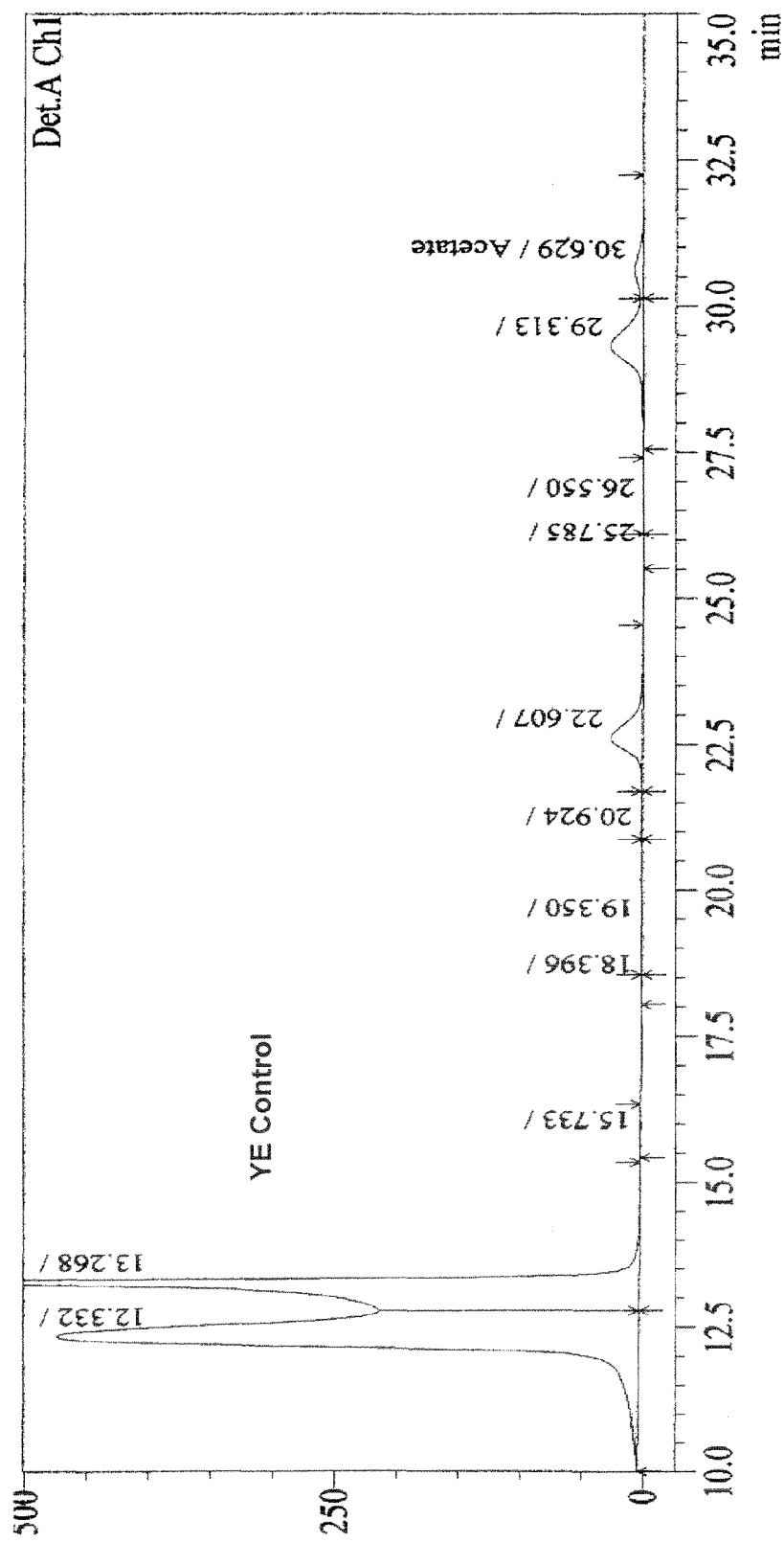
FIG. 12 illustrates the metabolic profile of the control from Example 3.

FIG. 9 shows that the absence of $CO_2$ headspace in the cellobiose cultures resulted in lower growth and about 20% less $H_2$ and acetate production, while also altering the metabolic profile, as shown in FIGS. 10-12. See also Table 2 below.

TABLE 2

Comparison of Growth Rate with and without $CO_2$

|  | $N_2$ | $N_2/CO_2$ |
|---|---|---|
| Hydrogen (μmol) | 223.0 ± 3.0 | 276.0 ± 13.0 |
| Acetate (mM) | 27.1 ± 0.5 | 35.0 ± 2.0 |
| Formate (mM) | 18.6 ± 0.4 | 18.0 ± 1.0 |
| Cellobiose (mM) | 1.2 ± 0.6 | 2.8 ± 0.7 |

Figure 13:
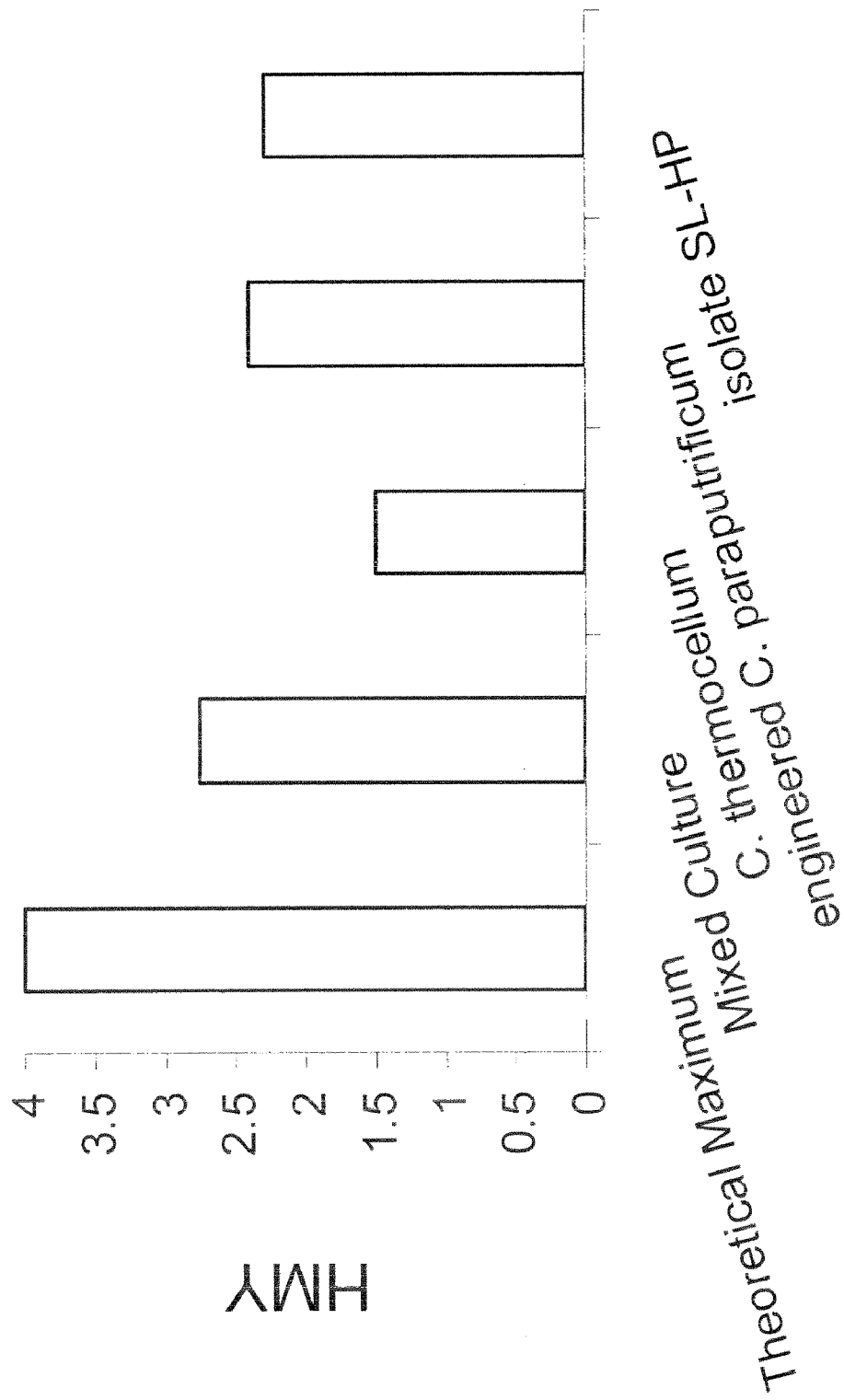
FIG. 13 depicts the hydrogen molar yields of several neutrophiles and isolated strain sapolanicus on cellobiose as compared to the theoretical maximum from Example 3.

The hydrogen molar yield of strain sapolanicus growing on cellobiose at pH>10 at 7% salinity (w/v) was then compared to the highest reported values of cells from C. thermocellum, and C. paraputrificum, and a mixed culture growing on glucose at pH 7. FIG. 13 shows the results of this comparison.

Example 4

Growth in Cellobiose with Agitation

In this Example, the growth and metabolic by-products of the cellobiose cultures prepared according to the procedures in Example 2 were measured under agitation and compared to the growth rate and by-products when not agitated. The cultures were agitated using a shaker at 250 rpm for a time period of 120 hours, while the growth rate and by-products were measured as described above in Example 3.

Figure 14:
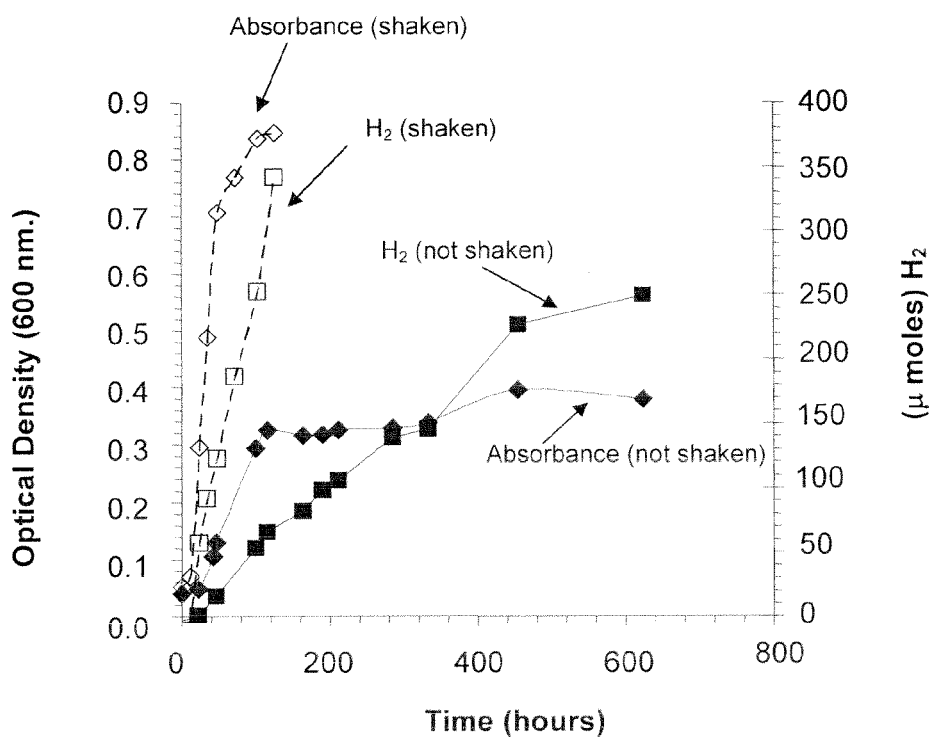
FIG. 14 is a graph comparing the growth rate and hydrogen production of isolated strain sapolanicus on cellobiose under cultivation conditions of agitation vs. not agitating the culture from Example 4.
Figure 15:
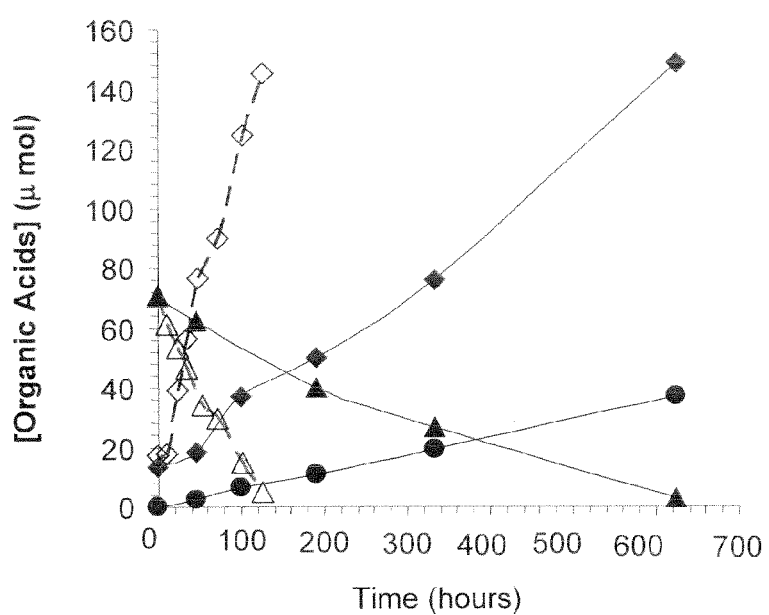
FIG. 15 is a graph comparing the by-product generation and cellobiose usage of isolated strain sapolanicus on cellobiose under cultivation conditions of agitation vs. not agitating the culture from Example 4.

As shown in FIG. 14, the agitation increased growth and $H_2$ production. As shown in FIG. 15, this also resulted in increased rates of cellobiose fermentation (shaken △ and not shaken ▲) and acetate production (shaken □ and not shaken ■). Formate (●) was no longer produced in the shaken cultures. The agitation decreased the generation time to about 12 hours and increased the biomass yield by 3-fold, while increasing the rate of $H_2$ production 5-fold and the overall $H_2$ yield by 30%. The results are also presented in Table 3 below.

TABLE 3

Effects of Agitation

|  | Agitation | No Agitation |
|---|---|---|
| HMY (μmol) | 2.3 ± 0.4 | 1.7 ± 0.2 |
| % $H_2$ headspace | 37.0 ± 4.0 | 26.0 ± 2.0 |

TABLE 3-continued

Effects of Agitation

|  | Agitation | No Agitation |
|---|---|---|
| $H_2$ Prod. Rate (mmol/L/h) | 0.57 | 0.07 |
| Acetate (mM) | 37.4 ± 2.0 | 31.0 ± 0.6 |
| Formate (mM) | 0 | 7.9 ± .06 |

Example 5

Biohydrogen Production from Switchgrass and Straw

In this Example, the growth and metabolic by-products of strain sapolanicus growing on switchgrass and straw were measured. Protein quantification, as previously described, was used for the determination of growth. The pH was maintained above 10.2 during incubation.

Switchgrass was obtained from the Bradford Farm at the University of Missouri and dried. The straw was purchased from a retail outlet and was already dried. Both were pulverized and passed through a 1 mm screen. The resulting lignocellulosic biomass material that passed through the screen was weighed out in 0.4 g aliquots and placed in 120 ml Pyrex serum bottles. Next, the lignocellulosic material was subjected to an alkaline pretreatment using 20 ml of a 40 g $Na_2CO_3/L$ solution to maintain a ratio of 20 g/L of lignocellulosic material. The bottles were then sealed with blue butyl rubber stoppers and crimp seals.

Digestion of the non-neutralized hemicellulosic liquor was tested with duplicate cultures using various pretreatment temperatures at ambient pressures. Pretreatment temperatures included room temperature (~20° C.; over night), 55° C. (2 hours), 75° C. (2 hours), 90° C. (1 hour), 130° C. (15 min.), 150° C. (15 min.), and 170° C. (15 min.) in a conventional oven. The pretreated samples were allowed to cool and then each transferred to 50 ml falcon tubes and centrifuged at 27,000×g for 12 minutes at room temperature.

Next, the supernatant and the insoluble slurry material were separated for determination of their respective capacities to support growth and biohydrogen production with strain SL-HP. The lignocellulosic liquor (supernatant) containing sugars resulting from hemicellulose was transferred to serum bottles, sealed with blue butyl stoppers and degassed with $N_2$.

Cultures were then prepared using the lignocellulosic liquor. First, 1 ml of filtered 5× concentrated medium solution described in Example 2 above was added to sterilized and anaerobic (80% $N_2$/20% $CO_2$) Balch/Hungate tubes without any carbon or electron source, followed by 3.5 ml of the degassed lignocellulosic liquor. The resulting 4.5 ml solution was then reduced with cysteine and sulfide as described above. Next, 0.5 ml of a freshly grown culture of strain SL-HP was added. The culture tubes were then incubated at 33° C. with shaking at 250 rpm. Before aliquoting to tubes, samples (1 ml) were taken for sugar and organic acid analysis as well as for protein quantification (0.3 ml) as described above. Similar samples were taken at the end of the cultivation, and the production of $H_2$ was followed periodically as described above.

Figure 16:
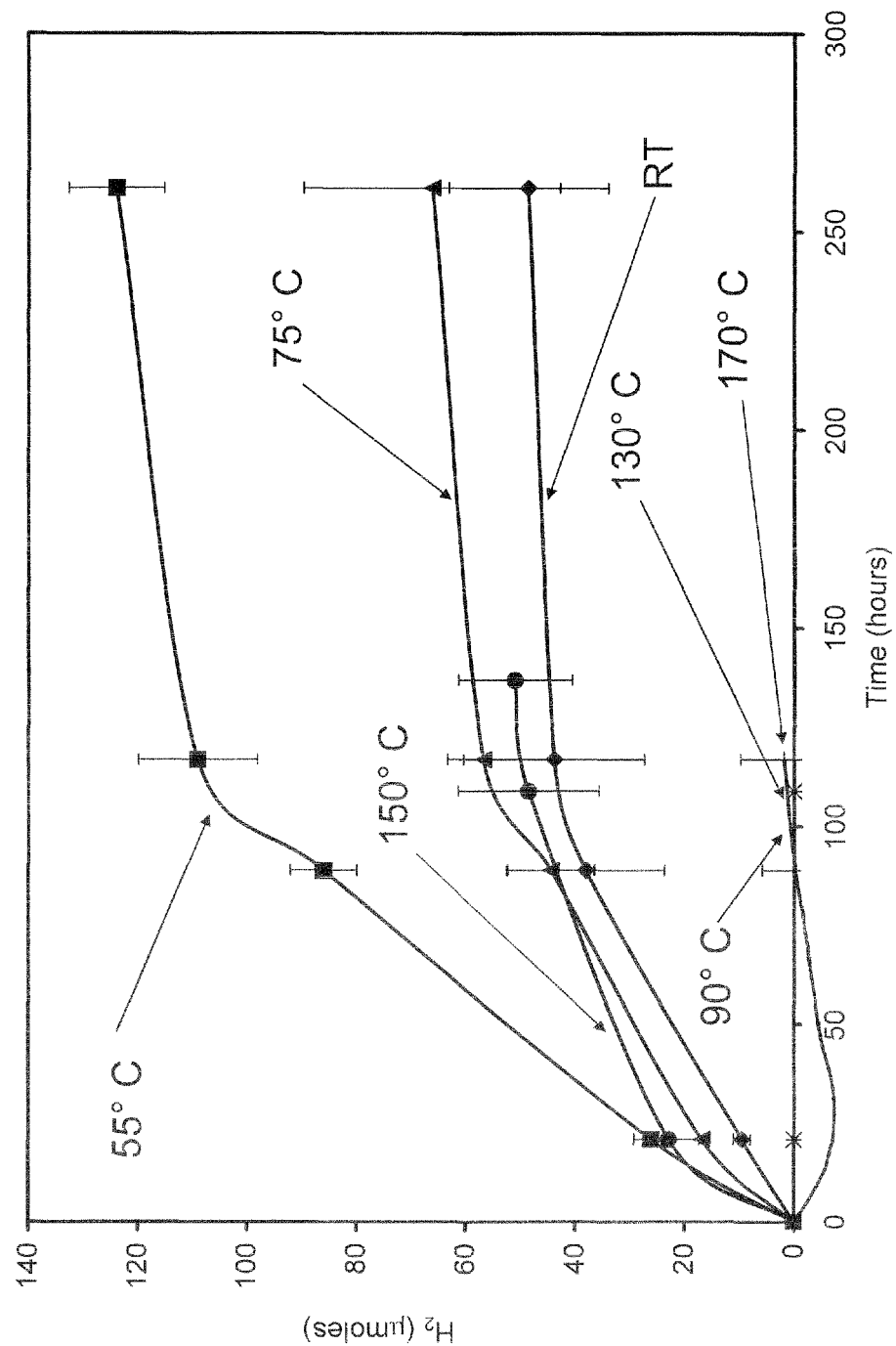
FIG. 16 is a graph of the biohydrogen production from the hemicellulosic liquor of switchgrass in Example 5.
Figure 17:
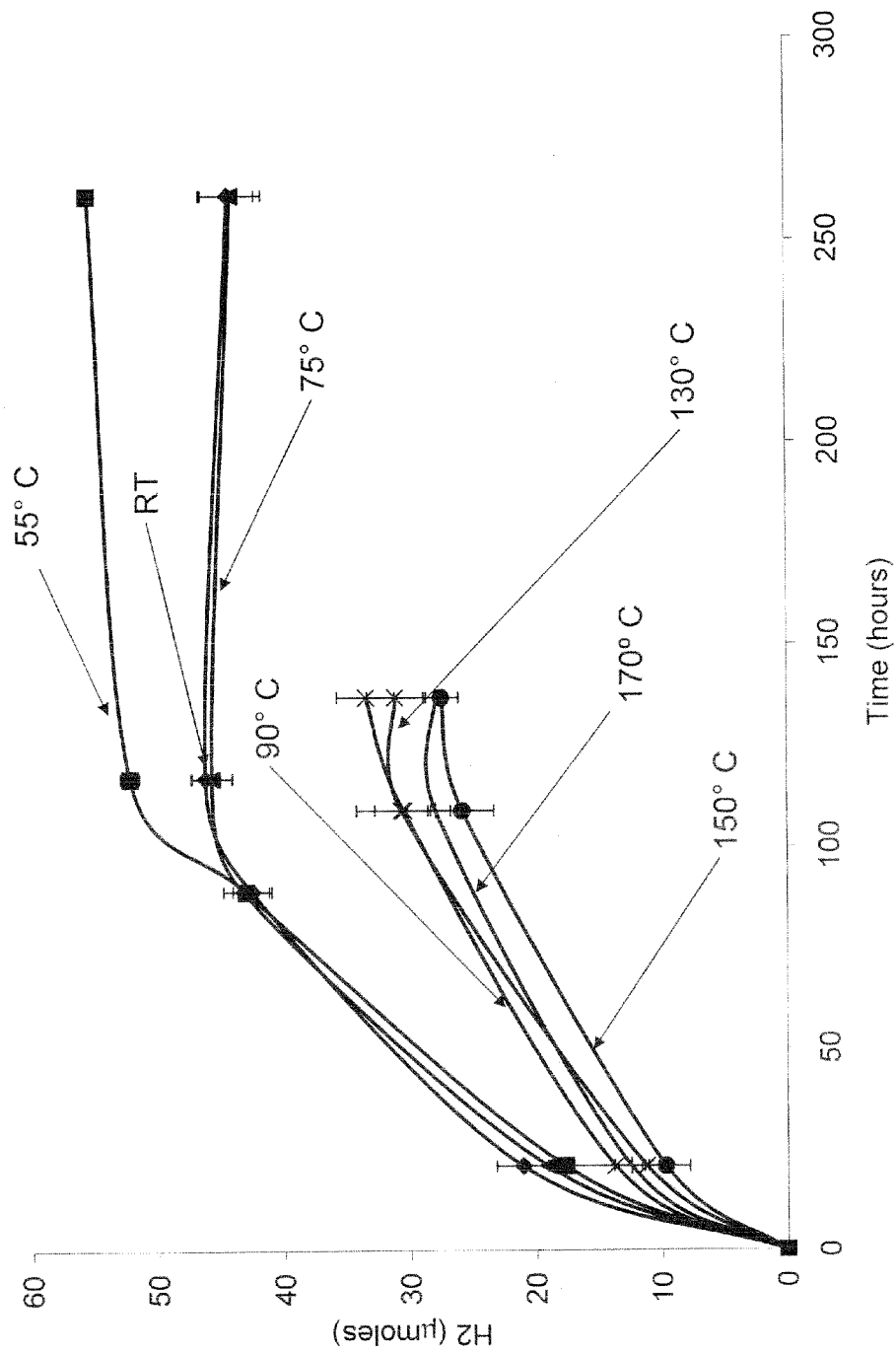
FIG. 17 is a graph of the biohydrogen production from the hemicellulosic liquor of straw in Example 5.

Cultures were also prepared using the insoluble slurry containing primarily cellulose. The slurry was first washed twice with 20 ml each of deionized and filter-sterilized water via centrifugation at 27,000×g for 12 minutes, at room temperature. The washed slurry was placed in pre-weighed plastic weighboats and dried at 80° C. for 2 hours, and weighed again when dry. Next, 0.2 grams of the dried solid material was added to sterile Balch/Hungate tubes, as described above, sealed, crimped and degassed (80% $N_2$/20% $CO_2$). Each tube then received 4.5 ml of filter-sterilized medium with no carbon or electron source, followed by 0.5 ml of a freshly grown culture of strain SL-HP. Immediately after inoculation, a replicate set of tubes was sacrificed to obtain samples for organic acid analysis (1 ml) as well as for protein quantification (0.3 ml) as described above. At the end of the cultivation, similar samples were taken, and the production of $H_2$ was followed periodically as described above. The results are depicted in FIG. 16 for switchgrass and FIG. 17 for straw.

Pretreatment at 55° C. (■) yielded higher $H_2$ concentrations than pretreatment at room temperature (♦), 75° C. (▲), 90° C. (x), 130° C. (*), 150° C. (●), or 170° C. (+). With each material protein concentrations in more than tripled by the end of the incubation for the room temperature and 55° C. pretreatments (approx. 22 µg/ml to 75 µg/ml). There was less than a 50% increase for the other pretreatment conditions. This was concomitant with the greatest production of acetate in both straw (6 mM at room temperature; 2.5 mM at 55° C.) and switchgrass (9 mM at room temperature, 14 mM at 55° C.), as measured by HPLC analysis.

The rates of biohydrogen production were 0.37 µmol $H_2$/hour/ml and 0.88 µmol $H_2$/hour/ml for straw and switchgrass, respectively, as compared to a range of 0.59 µmol $H_2$/hour/ml with xylose or arabinose, and up to 2.35 µmol $H_2$/hour/ml with glucose.

We claim:

1. An isolated, hydrogen-producing microorganism having a 16S rDNA sequence comprising SEQ ID NO: 1, or a sequence having at least 98% sequence homology with SEQ ID NO:1, said microorganism being haloalkaliphilic.

2. A method of producing hydrogen comprising fermenting a source of carbon with the microorganism of claim 1 in a culture medium.

3. The method of claim 2, wherein said fermenting is carried out at a pH of greater than or equal to about 10.

4. The method of claim 2, further comprising:
providing a quantity of biomass, sand biomass comprising stud source of carbon; and
pretreating said biomass prior to said fermenting to yield an aqueous pretreated biomass having a pH of greater than or equal to about 10.

5. The method of claim 4, wherein the pH of said pretreated biomass is not neutralized prior to said fermenting.

6. The method of claim 4, wherein said pretreated biomass has a salt content of from about 7% to about 7.5% w/v.

7. The method of claim 4, wherein said biomass is selected from the group consisting of seasonal grasses, agricultural products, saw dust, municipal solid waste, sugar processing waste, fruit processing waste, paper processing waste, and mixtures thereof.

8. The method of claim 4, wherein the pH during said fermenting is maintained at about 10.5 to about 11.

9. The method of claim 4, wherein said fermenting is carried out in a fermentation apparatus comprising said culture medium and said microorganism.

10. The method of claim 9, wherein said fermenting is carried out under substantially anaerobic conditions.

11. The method of claim 10, wherein said fermentation apparatus is provided with a headspace above said culture medium, said anaerobic conditions comprising providing a gas phase in said headspace, said gas phase being selected from the group consisting of $N_2$, $CO_2$, and mixtures thereof.

12. The method of claim 4, further comprising collecting hydrogen produced by said fermenting.

13. The method of claim 12, wherein said collecting comprises supplying said hydrogen to a hydrogen gas energy converting device.

14. The method of claim 4, further comprising:
collecting non-hydrogen by-products produced by said fermenting; and
supplying said non-hydrogen by-products to a photobioreactor.

* * * * *